US008450459B2

(12) United States Patent
Peschke et al.

(10) Patent No.: US 8,450,459 B2
(45) Date of Patent: May 28, 2013

(54) IL-21 DERIVATIVES AND VARIANTS

(75) Inventors: Bernd Peschke, Måløv (DK); Christine Bruun Schiødt, Brønshøj (DK); Helle Wöldike, Lynge (DK); Florencio Zaragoza Dörwald, Smørum (DK); Anne Worsaae, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/189,849

(22) Filed: Aug. 12, 2008

(65) Prior Publication Data

US 2009/0253864 A1 Oct. 8, 2009

Related U.S. Application Data

(63) Continuation of application No. 11/401,005, filed on Apr. 10, 2006, now abandoned, which is a continuation of application No. PCT/DK2004/000686, filed on Oct. 8, 2004.

(60) Provisional application No. 60/510,892, filed on Oct. 14, 2003, provisional application No. 60/513,422, filed on Oct. 22, 2003, provisional application No. 60/569,566, filed on May 10, 2004.

(30) Foreign Application Priority Data

Oct. 10, 2003 (DK) .................................. 2003 01496
Oct. 17, 2003 (DK) .................................. 2003 01529
May 4, 2004 (DK) .................................. 2004 00707

(51) Int. Cl.
*C07K 17/08* (2006.01)
*C07K 14/54* (2006.01)
*A61K 31/74* (2006.01)

(52) U.S. Cl.
USPC ............. 530/351; 530/815; 514/1.1; 514/3.2

(58) Field of Classification Search
None
See application file for complete search history.

(56) References Cited

U.S. PATENT DOCUMENTS

| | | | |
|---|---|---|---|
| 4,902,502 A | 2/1990 | Nitecki et al. | |
| 5,643,756 A * | 7/1997 | Kayman et al. | 435/69.7 |
| 6,307,024 B1 | 10/2001 | Novak et al. | |
| 6,423,685 B1 | 7/2002 | Drummond et al. | |
| 6,929,932 B2 | 8/2005 | Presnell et al. | |
| 6,946,261 B1 * | 9/2005 | Burian et al. | 435/69.1 |
| 7,186,805 B2 | 3/2007 | Presnell et al. | |
| 7,276,478 B2 | 10/2007 | Sivakumar et al. | |
| 7,528,104 B2 * | 5/2009 | Holmes et al. | 514/2 |
| 2003/0003545 A1 | 1/2003 | Ebner et al. | |
| 2003/0108549 A1 | 6/2003 | Carter et al. | |
| 2003/0186387 A1 | 10/2003 | Ebner et al. | |
| 2004/0009150 A1 * | 1/2004 | Nelson et al. | 424/85.2 |

FOREIGN PATENT DOCUMENTS

| | | |
|---|---|---|
| JP | 10-509208 | 9/1998 |
| JP | 2001-510033 | 7/2001 |
| JP | 2002-516103 | 6/2002 |
| JP | 2002-523333 | 7/2002 |
| JP | 2002-537839 | 11/2002 |
| JP | 2003-514517 | 4/2003 |
| JP | 2003-516322 | 5/2003 |
| JP | 2003-523390 | 8/2003 |
| JP | 2003-525628 | 9/2003 |
| JP | 2003-525908 | 9/2003 |
| JP | 2006-509525 | 3/2006 |
| JP | 2006-514601 | 5/2006 |
| JP | 2006-523682 | 10/2006 |
| JP | 2007-501812 | 2/2007 |
| JP | 2007-506789 | 3/2007 |
| JP | 2008-538290 | 10/2008 |
| WO | WO 90/07938 | 7/1990 |
| WO | WO 93/24138 A1 | 12/1993 |
| WO | WO 94/12219 | 6/1994 |
| WO | WO 96/40248 A1 | 12/1996 |
| WO | WO 96/41813 | 12/1996 |
| WO | WO 99/61617 | 12/1999 |
| WO | WO 00/07617 | 2/2000 |
| WO | WO 00/53761 | 9/2000 |
| WO | WO 01/35988 | 5/2001 |
| WO | WO 01/62252 | 8/2001 |
| WO | WO 01/66135 | 9/2001 |
| WO | WO 03/006501 | 1/2003 |
| WO | WO 03/040313 | 3/2003 |
| WO | WO 03/028630 | 4/2003 |
| WO | WO 03/038043 | 5/2003 |
| WO | WO 03/074566 | 9/2003 |
| WO | WO 2003/074567 | 9/2003 |
| WO | WO 03/082212 | 10/2003 |

(Continued)

OTHER PUBLICATIONS

Knauf et al. Relationship of effective molecular size to systemic clearance in rats of recombinant interleukin-2 chemically modified with water-soluble polymers. J Biol Chem. Oct. 15, 1988;263(29):15064-70.*

Parish-Novak J. et al., Nature (2000), vol. 408, No. 6808, pp. 57-63.

Collins M. et al., Immunologic Research (2003), vol. 28, No. 2, pp. 131-140.

Zalipsky S., Advanced Drug Delivery Reviews (1995), vol. 16, pp. 157-182.

Delgado C. et al., Critical Reviews in Therapeutic Drug Carrier Systems (1992), vol. 9, Nos. 3 and 4, pp. 249-304.

Katre N. V., Advanced Drug Delivery Reviews (1993), vol. 10, No. 1, pp. 91-114.

(Continued)

*Primary Examiner* — Dong Jiang
(74) *Attorney, Agent, or Firm* — Nelson Mullins Riley & Scarborough LLP; Jane E. Remillard, Esq.; Jeanne M. DiGiorgio

(57) ABSTRACT

The invention provides derivatives of IL-21 or variants thereof, methods of producing such variants, new variants of IL-21, and various methods of using such molecules.

7 Claims, No Drawings

FOREIGN PATENT DOCUMENTS

| WO | WO 03/087320 | 10/2003 |
|---|---|---|
| WO | WO 03/103589 | 12/2003 |
| WO | WO 03-103589 | 12/2003 |
| WO | WO 2004/055168 | 7/2004 |
| WO | WO 2004/084835 | 10/2004 |
| WO | WO 2004/112703 | 12/2004 |
| WO | WO 2005/014049 | 2/2005 |
| WO | WO 2005/030196 | 4/2005 |
| WO | WO 2005/052139 | 6/2005 |
| WO | WO 2006/111524 | 10/2006 |

OTHER PUBLICATIONS

Kinstler et al., Advanced Drug Delivery Reviews (2002), vol. 54, No. 4, pp. 477-485.

Communication from the EP Examining Division dated Jun. 3, 2009, issued in corresponding EP Application No. 04762905.0, 8 pages.

Response to the Jun. 3, 2009 Communication from the EP Examining Division dated Jan. 6, 2010, 6 pages.

Wei-Chiang, "Oral Peptide and Protein Delivery: Unfulfilled Promises?", Drug Discovery Today, Jul. 15, 2003, 8(14), 607-608.

Doerks et al., "Protein annotation: detective work for function prediction", Trends in Genetics, Jun. 1998, 14(6), 248-250.

Ngo et al., "Computational complexity, protein structure prediction, and the levinthal paradox", The Protein Folding Problems and Tertiary Structure Prediction, 1994, 492-495.

Skolnick et al., "From genes to protein structure and function: novel applications of computational approaches in the genomic era", Trends in Biotech, Jan. 2000, 18(1), 34-39.

Wells, "Additivity of Mutational Effects in Proteins", Biochemistry, Sep. 18, 1990, 29, 8509-8517.

Human Genome Sciences Inc., International Publication No. WO 03/060071, Jul. 24, 2003, http://www.wipo.int/patentscope/search/en/detail.jsf?docId=WO2003060071&recNum=1&tab=PCTDocuments&maxRec=1&office=&prevFilter=&sortOption=&queryString=FP%3A%28WO03060071%29, 598 pages.

Stennicke et al., "C-Terminal Incorporation of Fluorganic and Affinity Labels Using Wild-Type and Mutagenized Carboxypeptidase Y", Analytical Biochemistry, May 1997, vol. 248, Issue 1, 141-148.

* cited by examiner

SEQUENCE LISTING

```
<160> NUMBER OF SEQ ID NOS: 21

<210> SEQ ID NO 1
<211> LENGTH: 642
<212> TYPE: DNA
<213> ORGANISM: Homo sapiens
```

```
<220> FEATURE:
<221> NAME/KEY: CDS
<222> LOCATION: (47)..(532)

<400> SEQUENCE: 1
gctgaagtga aaacgagacc aaggtctagc tctactgttg gtactt atg aga tcc        55
                                                Met Arg Ser
                                                 1 agt cct ggc aac atg gag agg att gtc atc tgt ctg atg gtc atc ttc      103
Ser Pro Gly Asn Met Glu Arg Ile Val Ile Cys Leu Met Val Ile Phe
  5              10                  15 ttg ggg aca ctg gtc cac aaa tca agc tcc caa ggt caa gat cgc cac      151
Leu Gly Thr Leu Val His Lys Ser Ser Ser Gln Gly Gln Asp Arg His
 20                  25                  30                  35 atg att aga atg cgt caa ctt ata gat att gtt gat cag ctg aaa aat      199
Met Ile Arg Met Arg Gln Leu Ile Asp Ile Val Asp Gln Leu Lys Asn
                 40                  45                  50 tat gtg aat gac ttg gtc cct gaa ttt ctg cca gct cca gaa gat gta      247
Tyr Val Asn Asp Leu Val Pro Glu Phe Leu Pro Ala Pro Glu Asp Val
             55                  60                  65 gag aca aac tgt gag tgg tca gct ttt tcc tgt ttt cag aag gcc caa      295
Glu Thr Asn Cys Glu Trp Ser Ala Phe Ser Cys Phe Gln Lys Ala Gln
         70                  75                  80 cta aag tca gca aat aca gga aac aat gaa agg ata atc aat gta tca      343
Leu Lys Ser Ala Asn Thr Gly Asn Asn Glu Arg Ile Ile Asn Val Ser
     85                  90                  95 att aaa aag ctg aag agg aaa cca cct tcc aca aat gca ggg aga aga      391
Ile Lys Lys Leu Lys Arg Lys Pro Pro Ser Thr Asn Ala Gly Arg Arg
100                 105                 110                 115 cag aaa cac aga cta aca tgc cct tca tgt gat tct tat gag aaa aaa      439
Gln Lys His Arg Leu Thr Cys Pro Ser Cys Asp Ser Tyr Glu Lys Lys
                120                 125                 130 cca ccc aaa gaa ttc cta gaa aga ttc aaa tca ctt ctc caa aag atg      487
Pro Pro Lys Glu Phe Leu Glu Arg Phe Lys Ser Leu Leu Gln Lys Met
            135                 140                 145 att cat cag cat ctg tcc tct aga aca cac gga agt gaa gat tcc          532
Ile His Gln His Leu Ser Ser Arg Thr His Gly Ser Glu Asp Ser
        150                 155                 160 tgaggatcta acttgcagtt ggacactatg ttacatactc taatatagta gtgaaagtca    592
tttctttgta ttccaagtgg aggagcccta ttaaattata taaagaaata               642

<210> SEQ ID NO 2
<211> LENGTH: 162
<212> TYPE: PRT
<213> ORGANISM: Homo sapiens

<400> SEQUENCE: 2

Met Arg Ser Ser Pro Gly Asn Met Glu Arg Ile Val Ile Cys Leu Met
 1               5                  10                  15

Val Ile Phe Leu Gly Thr Leu Val His Lys Ser Ser Ser Gln Gly Gln
             20                  25                  30

Asp Arg His Met Ile Arg Met Arg Gln Leu Ile Asp Ile Val Asp Gln
         35                  40                  45

Leu Lys Asn Tyr Val Asn Asp Leu Val Pro Glu Phe Leu Pro Ala Pro
     50                  55                  60

Glu Asp Val Glu Thr Asn Cys Glu Trp Ser Ala Phe Ser Cys Phe Gln
 65                  70                  75                  80

Lys Ala Gln Leu Lys Ser Ala Asn Thr Gly Asn Asn Glu Arg Ile Ile
                 85                  90                  95
```

-continued

Asn Val Ser Ile Lys Lys Leu Lys Arg Lys Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 3
<211> LENGTH: 260
<212> TYPE: PRT
<213> ORGANISM: Homo sapiens

<400> SEQUENCE: 3

Met Lys Phe Leu Val Asn Val Ala Leu Val Phe Met Val Val Tyr Ile
1               5                   10                  15

Ser Tyr Ile Tyr Ala Gly Ser Gly His His His His His His Gly Ser
            20                  25                  30

Gly Asp Tyr Lys Asp Asp Asp Asp Lys Gly Ser Gly Cys Pro Asp Leu
        35                  40                  45

Val Cys Tyr Thr Asp Tyr Leu Gln Thr Val Ile Cys Ile Leu Glu Met
    50                  55                  60

Trp Asn Leu His Pro Ser Thr Leu Thr Leu Thr Trp Gln Asp Gln Tyr
65                  70                  75                  80

Glu Glu Leu Lys Asp Glu Ala Thr Ser Cys Ser Leu His Arg Ser Ala
                85                  90                  95

His Asn Ala Thr His Ala Thr Tyr Thr Cys His Met Asp Val Phe His
            100                 105                 110

Phe Met Ala Asp Asp Ile Phe Ser Val Asn Ile Thr Asp Gln Ser Gly
        115                 120                 125

Asn Tyr Ser Gln Glu Cys Gly Ser Phe Leu Leu Ala Glu Ser Ile Lys
    130                 135                 140

Pro Ala Pro Pro Phe Asn Val Thr Val Thr Phe Ser Gly Gln Tyr Asn
145                 150                 155                 160

Ile Ser Trp Arg Ser Asp Tyr Glu Asp Pro Ala Phe Tyr Met Leu Lys
                165                 170                 175

Gly Lys Leu Gln Tyr Glu Leu Gln Tyr Arg Asn Arg Gly Asp Pro Trp
            180                 185                 190

Ala Val Ser Pro Arg Arg Lys Leu Ile Ser Val Asp Ser Arg Ser Val
        195                 200                 205

Ser Leu Leu Pro Leu Glu Phe Arg Lys Asp Ser Ser Tyr Glu Leu Gln
    210                 215                 220

Val Arg Ala Gly Pro Met Pro Gly Ser Ser Tyr Gln Gly Thr Trp Ser
225                 230                 235                 240

Glu Trp Ser Asp Pro Val Ile Phe Gln Thr Gln Ser Glu Glu Leu Lys
                245                 250                 255

Glu Gly Trp Asn
            260

<210> SEQ ID NO 4
<211> LENGTH: 467
<212> TYPE: PRT
<213> ORGANISM: Homo sapiens

<400> SEQUENCE: 4

```
Met Pro Arg Gly Trp Ala Ala Pro Leu Leu Leu Leu Leu Gln Gly
1               5                   10                  15

Gly Trp Gly Cys Pro Asp Leu Val Cys Tyr Thr Asp Tyr Leu Gln Thr
                20                  25                  30

Val Ile Cys Ile Leu Glu Met Trp Asn Leu His Pro Ser Thr Leu Thr
            35                  40                  45

Leu Thr Trp Gln Asp Gln Tyr Glu Glu Leu Lys Asp Glu Ala Thr Ser
50                      55                      60

Cys Ser Leu His Arg Ser Ala His Asn Ala Thr His Ala Thr Tyr Thr
65                  70                      75                  80

Cys His Met Asp Val Phe His Phe Met Ala Asp Ile Phe Ser Val
                85                  90                  95

Asn Ile Thr Asp Gln Ser Gly Asn Tyr Ser Gln Glu Cys Gly Ser Phe
                100                 105                 110

Leu Leu Ala Glu Ser Ile Lys Pro Ala Pro Pro Phe Asn Val Thr Val
            115                 120                 125

Thr Phe Ser Gly Gln Tyr Asn Ile Ser Trp Arg Ser Asp Tyr Glu Asp
130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
                195                 200                 205

Ser Tyr Gln Gly Thr Trp Ser Glu Trp Ser Asp Pro Val Ile Phe Gln
210                 215                 220

Thr Gln Ser Glu Glu Leu Lys Glu Gly Trp Asn Gly Ser Gly Ser Arg
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
        290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Val Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415
```

-continued

```
Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 5
<211> LENGTH: 492
<212> TYPE: PRT
<213> ORGANISM: Homo sapiens

<400> SEQUENCE: 5

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Gly Ser Gly Ser Arg
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320
```

-continued

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Val Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Ser Gly Met Ala Ser Met Thr Gly Gly Gln Gln Met Gly
465                 470                 475                 480

Ser Gly Ser His His His His His His Ser Gly Gly
                485                 490

<210> SEQ ID NO 6
<211> LENGTH: 467
<212> TYPE: PRT
<213> ORGANISM: Homo sapiens

<400> SEQUENCE: 6

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

```
Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Gly Ser Gly Ser Arg
225                 230                 235                 240

Asp Lys Thr His Thr Cys Pro Cys Pro Ala Pro Glu Ala Leu Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 7
<211> LENGTH: 245
<212> TYPE: PRT
<213> ORGANISM: Homo sapiens

<400> SEQUENCE: 7

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
                20                  25                  30

Val Ile Cys Ile Leu Glu Met Trp Asn Leu His Pro Ser Thr Leu Thr
            35                  40                  45

Leu Thr Trp Gln Asp Gln Tyr Glu Glu Leu Lys Asp Glu Ala Thr Ser
        50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110
```

```
Leu Leu Ala Glu Ser Ile Lys Pro Ala Pro Pro Phe Asn Val Thr Val
            115                 120                 125

Thr Phe Ser Gly Gln Tyr Asn Ile Ser Trp Arg Ser Asp Tyr Glu Asp
        130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
210                 215                 220

Thr Gln Ser Glu Glu Leu Lys Glu Gly Trp Asn Lys Thr Glu Thr Ser
225                 230                 235                 240

Gln Val Ala Pro Ala
            245

<210> SEQ ID NO 8
<211> LENGTH: 470
<212> TYPE: PRT
<213> ORGANISM: Homo sapiens

<400> SEQUENCE: 8

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Asp Asp Asp Lys
225                 230                 235                 240
```

```
Gly Ser Gly Asp Lys Thr His Thr Cys Pro Cys Pro Ala Pro Glu
                245                 250                 255

Ala Leu Gly Ala Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 9
<211> LENGTH: 240
<212> TYPE: PRT
<213> ORGANISM: Mus musculus

<400> SEQUENCE: 9

Met Pro Arg Gly Pro Val Ala Ala Leu Leu Leu Ile Leu His Gly
1               5                   10                  15

Ala Trp Ser Cys Leu Asp Leu Thr Cys Tyr Thr Asp Tyr Leu Trp Thr
            20                  25                  30

Ile Thr Cys Val Leu Glu Thr Arg Ser Pro Asn Pro Ser Ile Leu Ser
        35                  40                  45

Leu Thr Trp Gln Asp Glu Tyr Glu Glu Leu Gln Asp Gln Glu Thr Phe
    50                  55                  60

Cys Ser Leu His Arg Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140
```

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
            165                 170                 175

Ser Val Asp Ser Arg Asn Val Ser Leu Leu Pro Glu Glu Phe His Lys
        180                 185                 190

Asp Ser Ser Tyr Gln Leu Gln Val Arg Ala Ala Pro Gln Pro Gly Thr
    195                 200                 205

Ser Phe Arg Gly Thr Trp Ser Glu Trp Ser Asp Pro Val Ile Phe Gln
210                 215                 220

Thr Gln Ala Gly Glu Pro Glu Ala Gly Trp Asp Gly Ser Gly Ser Arg
225                 230                 235                 240

<210> SEQ ID NO 10
<211> LENGTH: 255
<212> TYPE: PRT
<213> ORGANISM: Mus musculus

<400> SEQUENCE: 10

Met Pro Arg Gly Pro Val Ala Ala Leu Leu Leu Ile Leu His Gly
1               5                   10                  15

Ala Trp Ser Cys Leu Asp Leu Thr Cys Tyr Thr Asp Tyr Leu Trp Thr
                20                  25                  30

Ile Thr Cys Val Leu Glu Thr Arg Ser Pro Asn Pro Ser Ile Leu Ser
            35                  40                  45

Leu Thr Trp Gln Asp Glu Tyr Glu Glu Leu Gln Asp Gln Glu Thr Phe
    50                  55                  60

Cys Ser Leu His Arg Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
    115                 120                 125

Ala Phe Ser Gly Arg Tyr Asp Ile Ser Trp Asp Ser Ala Tyr Asp Glu
130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
            165                 170                 175

Ser Val Asp Ser Arg Asn Val Ser Leu Leu Pro Glu Glu Phe His Lys
        180                 185                 190

Asp Ser Ser Tyr Gln Leu Gln Val Arg Ala Ala Pro Gln Pro Gly Thr
    195                 200                 205

Ser Phe Arg Gly Thr Trp Ser Glu Trp Ser Asp Pro Val Ile Phe Gln
210                 215                 220

Thr Gln Ala Gly Glu Pro Glu Ala Gly Trp Asp Gly Ser Gly His His
225                 230                 235                 240

His His His His Gly Ser Gly Asp Tyr Lys Asp Asp Asp Lys
                245                 250                 255

<210> SEQ ID NO 11
<211> LENGTH: 260
<212> TYPE: PRT
<213> ORGANISM: Mus musculus -continued

<400> SEQUENCE: 11

```
Met Lys Phe Leu Val Asn Val Ala Leu Val Phe Met Val Val Tyr Ile
1               5                   10                  15

Ser Tyr Ile Tyr Ala Gly Ser Gly His His His His His His Gly Ser
            20                  25                  30

Gly Asp Tyr Lys Asp Asp Asp Asp Lys Gly Ser Gly Cys Leu Asp Leu
        35                  40                  45

Thr Cys Tyr Thr Asp Tyr Leu Trp Thr Ile Thr Cys Val Leu Glu Thr
    50                  55                  60

Arg Ser Pro Asn Pro Ser Ile Leu Ser Leu Thr Trp Gln Asp Glu Tyr
65                  70                  75                  80

Glu Glu Leu Gln Asp Gln Glu Thr Phe Cys Ser Leu His Arg Ser Gly
                85                  90                  95

His Asn Thr Thr His Ile Trp Tyr Thr Cys His Met Arg Leu Ser Gln
            100                 105                 110

Phe Leu Ser Asp Glu Val Phe Ile Val Asn Val Thr Asp Gln Ser Gly
        115                 120                 125

Asn Asn Ser Gln Glu Cys Gly Ser Phe Val Leu Ala Glu Ser Ile Lys
130                 135                 140

Pro Ala Pro Pro Leu Asn Val Thr Val Ala Phe Ser Gly Arg Tyr Asp
145                 150                 155                 160

Ile Ser Trp Asp Ser Ala Tyr Asp Glu Pro Ser Asn Tyr Val Leu Arg
                165                 170                 175

Gly Lys Leu Gln Tyr Glu Leu Gln Tyr Arg Asn Leu Arg Asp Pro Tyr
            180                 185                 190

Ala Val Arg Pro Val Thr Lys Leu Ile Ser Val Asp Ser Arg Asn Val
        195                 200                 205

Ser Leu Leu Pro Glu Glu Phe His Lys Asp Ser Ser Tyr Gln Leu Gln
210                 215                 220

Val Arg Ala Ala Pro Gln Pro Gly Thr Ser Phe Arg Gly Thr Trp Ser
225                 230                 235                 240

Glu Trp Ser Asp Pro Val Ile Phe Gln Thr Gln Ala Gly Glu Pro Glu
                245                 250                 255

Ala Gly Trp Asp
            260
```

<210> SEQ ID NO 12
<211> LENGTH: 147
<212> TYPE: PRT
<213> ORGANISM: Artificial Sequence
<220> FEATURE:
<223> OTHER INFORMATION: Description of Artificial Sequence: Synthetic
      zalpha11 ligand Q153ST/I156D polypeptide

<400> SEQUENCE: 12

```
Met Asp Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80
```

-continued

```
Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Asp Lys Met
145
```

<210> SEQ ID NO 13
<211> LENGTH: 162
<212> TYPE: PRT
<213> ORGANISM: Artificial Sequence
<220> FEATURE:
<223> OTHER INFORMATION: Description of Artificial Sequence: Synthetic
      zalpha11 ligand Q153D/I156D polypeptide

<400> SEQUENCE: 13

```
Met Asp Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Asp Lys Met Asp His Gln His Leu Ser Ser Arg Thr His Gly Ser Glu
145                 150                 155                 160

Asp Ser
```

<210> SEQ ID NO 14
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Gln Gly Gln Asp Arg His Met Ile Arg Met Arg Gln Leu Ile Asp
1               5                   10                  15

Ile Val Asp Gln Leu Lys Asn Tyr Val Asn Asp Leu Val Pro Glu Phe
            20                  25                  30

Leu Pro Ala Pro Glu Asp Val Glu Thr Asn Cys Glu Trp Ser Ala Phe
        35                  40                  45

Ser Cys Phe Gln Lys Ala Gln Leu Lys Ser Ala Asn Thr Gly Asn Asn
    50                  55                  60
```

Glu Arg Ile Ile Asn Val Ser Ile Lys Lys Leu Lys Arg Lys Pro Pro
65                  70                  75                  80

Ser Thr Asn Ala Gly Arg Arg Gln Lys His Arg Leu Thr Cys Pro Ser
                85                  90                  95

Cys Asp Ser Tyr Glu Lys Lys Pro Pro Lys Glu Phe Leu Glu Arg Phe
            100                 105                 110

Lys Ser Leu Leu Gln Lys Met Ile His Gln His Leu Ser Ser Arg Thr
        115                 120                 125

His Gly Ser Glu Asp Ser
    130

<210> SEQ ID NO 15
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Glu Ala Glu
1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Ser Glu Ala Glu
1               5

```
<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: This sequence may contain 1 to 5 residues.
<220> FEATURE:
<223> OTHER INFORMATION: C-term PEG

<400> SEQUENCE: 18

Gly Gly Gly Gly Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: This sequence may contain 1 to 5 residues.
<220> FEATURE:
<223> OTHER INFORMATION: C-term lipid

<400> SEQUENCE: 19

Gly Gly Gly Gly Gly
1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: This sequence may contain 1 to 4 residues.
<220> FEATURE:
<223> OTHER INFORMATION: C-term -NH-CH2-CHO

<400> SEQUENCE: 20

Gly Gly Gly Gly
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: This sequence may contain 1 to 4 residues.
<220> FEATURE:
<223> OTHER INFORMATION: C-term -NH-CH2-C-O-NH2

<400> SEQUENCE: 21

Gly Gly Gly Gly
1
```

IL-21 DERIVATIVES AND VARIANTS

CROSS-REFERENCE TO RELATED PATENT APPLICATIONS

This patent application is a continuation of U.S. patent application Ser. No. 11/401,005, filed Apr. 10, 2006, now abandoned, which is a continuation of International Application PCT/DK2004/000686, filed Oct. 8, 2004, which claims the benefit of U.S. Provisional Patent Application Nos. 60/510,892, filed Oct. 14, 2003, 60/513,422, filed Oct. 22, 2003 and 60/569,566, filed May 10, 2004 and Danish Patent Application Nos. PA 2003 01496, filed Oct. 10, 2003, PA 2003 01529, filed Oct. 17, 2003 and PA 2004 00707, filed May 4, 2004.

FIELD OF THE INVENTION

The invention relates to derivatives of interleukin 21 (IL-21) and IL-21 variants, as well as the synthesis and purification of derivatives of IL-21 and analogues thereof (including variants of IL-21 which act as IL-21 antagonists).

BACKGROUND OF THE INVENTION

IL-21 was described for example in WO 00/53761 as a stimulator of T cell growth and NK activity. Derivatives of IL-21 have previously not been described. As a potent pharmaceutical derivatives with modified characteristics are interesting in many applications.

SUMMARY OF THE INVENTION

The invention provides derivatives of IL-21 or variants thereof.

In an aspect the invention provides derivatives of IL-21 or variants thereof which comprises a polymeric molecule or lipophilic derivative (substituent).

In an aspect of the invention the derivative of IL-21 or variants thereof, comprises a polymeric molecule which is one or more PEG groups.

In an aspect of the invention derivatives of IL-21 or variants thereof, comprises derivatisation in the N-terminal, or the C-terminal or internally in the molecule.

In an aspect of the invention the derivatisation is on a naturally occurring amino acid and/or one or more amino acid added or substituted into the IL-21 sequence.

The invention provides the specific variant Ser-hIL21, isolated DNA expressing the specific variant and the use for derivatisation with a polymeric molecule. The invention also provides the use of the derivatives of IL-21 or variants thereof, for the manufacture of a medicament for the treatment of cancer of infectious diseases.

DESCRIPTION OF THE INVENTION

The invention provides various derivatives of the IL-21 peptides. The derivatives include chemically modified peptides that comprise an IL-21 peptide, or variants of the IL-21 peptide. Chemical modification may alter the chemical and biological characteristics of a molecule dependent on the characteristics of the derivatising molecule. The effect of modification may be maintaining the biological function of the peptide or potentially a lower activity of the peptide. For example derivatisation may extend the functional in vivo half life of a derivatised peptide and thus compensate for a lower activity. For example a protracted profile effect of IL-21 derivatives may be achieved by coupling of a IL-21 peptide or an analogue thereof to a hydrophilic moiety that results in IL-21 derivatives with a maintained biological activity. The derivatisation may for example provide a peptide with an improved half-life, thereby facilitating the continuous presence of therapeutically effective amount of IL-21 or a derivative thereof having the same biological effect. The amount needed for administration of an effective amount of a protracted peptide may thus be lower. Derivatisation may protect the molecule against degradation by enzymes and prevent clearance from the body. The derivatisation is preferably non-immugenic. In an aspect of the invention the solubility of the peptide may be amended.

IL-21 activity is as defined as described in Parrish-Novak, Nature, 408, 57-63, 2000; Brady, J., Hayakawa, Y., Smyth, M. J., and Nutt, S. L. 2004. IL-21 induces the functional maturation of murine NK cells. *Journal of immunology* (Baltimore, Md. 172:2048-2058; Collins, M., Whitters, M. J., and Young, D. A. 2003. IL-21 and IL-21 receptor: a new cytokine pathway modulates innate and adaptive immunity. *Immunol Res* 28:131-140; Habib, T., Nelson, A., and Kaushansky, K. 2003. IL-21: a novel IL-2-family lymphokine that modulates B, T, and natural killer cell responses. *J Allergy Clin Immunol* 112:1033-1045. Sivakumar, P. V. 2004. Interleukin-21 is a T-helper cytokine that regulates humoral immunity and cell-mediated anti-tumour responses. *Immunology* 112:177; Wang, G., Tschoi, M., Spolski, R., Lou, Y., Ozaki, K., Feng, C., Kim, G., Leonard, W. J., and Hwu, P. 2003. In vivo antitumor activity of interleukin 21 mediated by natural killer cells. *Cancer Res* 63:9016-9022; Wang, G. 2003. In vivo antitumor activity of interleukin 21 mediated by natural killer cells. *Cancer Res* 63:9016. IL-21 and derivatives thereof are considered useful in the treatment of neoplastic disorders. Neoplastic disorders or cancer are to be understood as referring to all forms of neoplastic cell growth, including both cystic and solid tumors, bone and soft tissue tumors, including both benign and malignant tumors, including tumors in anal tissue, bile duct, bladder, blood cells, bone, bone (secondary), bowel (colon & rectum), brain, brain (secondary), breast, breast (secondary), carcinoid, cervix, children's cancers, eye, gullet (oesophagus), head & neck, kaposi's sarcoma, kidney, larynx, leukaemia (acute lymphoblastic), leukaemia (acute myeloid), leukaemia (chronic lymphocytic), leukaemia (chronic myeloid), leukaemia (other), liver, liver (secondary), lung, lung (secondary), lymph nodes (secondary), lymphoma (hodgkin's), lymphoma (non-hodgkin's), melanoma, mesothelioma, myeloma, ovary, pancreas, penis, prostate, skin, soft tissue sarcomas, stomach, testes, thyroid, unknown primary tumor, vagina, vulva, womb (uterus). Soft tissue tumors include Benign schwannoma Monosomy, Desmoid tumor, Lipo-blastoma, Lipoma, Uterine leiomyoma, Clear cell sarcoma, Dermatofibrosarcoma, Ewing sarcoma, Extraskeletal myxoid chondrosarcoma, Liposarcoma myxoid, Liposarcoma, well differentiated, Alveolar rhabdomyosarcoma, and Synovial sarcoma. Specific bone tumor include Nonossifying Fibroma, Unicameral bone cyst, Enchondroma, Aneurysmal bone cyst, Osteoblastoma, Chondroblastoma, Chondromyxofibroma, Ossifying fibroma and Adamantinoma, Giant cell tumor, Fibrous dysplasia, Ewing's Sarcoma, Eosinophilic Granuloma, Osteosarcoma, Chondroma, Chondrosarcoma, Malignant Fibrous Histiocytoma, and Metastatic Carcinoma. Leukaemias refers to cancers of the white blood cells which are produced by the bone marrow. This includes but are not limited to the four main types of leukaemia; acute lymphoblastic (ALL), acute myeloblastic (AML), chronic lymphocytic (CLL) and chronic myeloid (CML).

Prior to a discussion of the detailed embodiments of the invention, a definition of specific terms related to the main aspects of the invention is provided.

In the context of the present invention IL-21 is defined as the sequence disclosed in WO00/53761 as SEQ ID NO:2, or the same sequence without the N-terminal sequence. The present application also describes variants and derivatives of IL-21. In the context of the present invention the term "IL-21" thus means IL-21 as described in WO0/53761 optionally without the N-terminal sequence. The present invention embraces counterpart proteins and from other species ("orthologs"). Of particular interest are IL-21 polypeptides from other mammalian species, including rodent, porcine, ovine, bovine, canine, feline, equine, and other primates.

"IL-21 derivatives" comprises derivatisation or linking to another functional molecule. The linking can be chemical coupling, genetic fusion, non-covalent association or the like, to other molecular entities such as antibodies, toxins, radio-isotope, cytotoxic or cytostatic agents or polymeric molecules or lipophilic groups. Non-limiting examples include polymeric groups such as, e.g, dendrimers as disclosed in PCT/DK2004/000531, polyalkylene oxide (PAO), polyalkylene glycol (PAG), polyethylene glycol (PEG), polypropylene glycol (PPG), branched PEGs, polyvinyl alcohol (PVA), polycarboxylate, poly-vinylpyrrolidone, polyethylene-co-maleic acid anhydride, polystyrene-co-maleic acid anhydride, dextran, carboxymethyl-dextran; serum protein binding-ligands, such as compounds which bind to albumin, like fatty acids, $C_5$-$C_{24}$ fatty acid, aliphatic diacid (e.g. $C_5$-$C_{24}$). Albumin binders are described in Danish patent applications PCT/DK04/000625. Albumin binders are also compounds of the following formula:

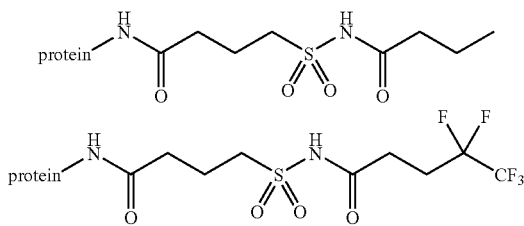

Other examples of protracting groups includes small organic molecules containing moieties that under physiological conditions alters charge properties, such as carboxylic acids or amines, or neutral substituents that prevent glycan specific recognition such as smaller alkyl substituents (e.g., $C_1$-$C_5$ alkyl).

Variants or analogues of IL-21 peptides are characterized as having one or more amino acid substitutions, deletions or additions. These changes are typically of a minor nature, that is conservative amino acid substitutions and other substitutions that do not significantly affect the receptor binding, receptor affinity, folding or biological activity of the peptide; However, as described below even small amendments in essential amino acids changes the effect of the IL-21 peptide. Small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, protein A, Nilsson et al., EMBO J. 4:1075 (1985); Nilsson et al., Methods Enzymol. 198:3 (1991), glutathione S transferase, Smith and Johnson, Gene 67:31 (1988), or other antigenic epitope or binding domain. See, in general Ford et al., Protein Expression and Purification 2: 95-107 (1991). DNAs encoding affinity tags are available from commercial suppliers (e.g., Pharmacia Biotech, Piscataway, N.J.). Variants of IL-21 peptides may also comprise non-naturally occurring amino acid residues. Non-naturally occurring amino acids include, without limitation, trans-3-methylproline, 2,4-methanoproline, cis-4-hydroxyproline, trans-4-hydroxyproline, Nmethylglycine, addo-threonine, methylthreonine, hydroxyethylcysteine, hydroxyethylhomocysteine, nitroglutamine, homoglutamine, pipecolic acid, thiazolidine carboxylic acid, dehydroproline, 3-and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating nonnaturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Essential amino acids in the polypeptides of the present invention can be identified according to procedures known in the art, such as site-directed mutagenesis or alaninescanning mutagenesis [Cunningham and Wells, Science 244: 1081-1085 (1989)]; Bass et al., Proc. Natl. Acad. Sci. USA 88:4498-4502 (1991). In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-protein interaction can also be determined by analysis of crystal structure as determined by such techniques as nuclear magnetic resonance, crystallography or photoaffinity labeling. The identities of essential amino acids can also be inferred from analysis of homologies with related proteins.

In one embodiment a variant is 70% or more identical with the sequence of SEQ ID NO:2 of WO0053761 (SEQ ID NO:2 of this disclosure). In one embodiment a variant is 80% or more identical with the SEQ ID NO:2 of WO0053761 (SEQ ID NO:2 of this disclosure). In another embodiment a variant is 90% or more identical with the sequence of SEQ ID NO:2 of WO0053761 (SEQ ID NO:2 of this disclosure). In a further embodiment a variant is 95% or more identical with the sequence of SEQ ID NO:2 of WO0053761 (SEQ ID NO:2 of this disclosure).

Percentage sequence identity between two amino acid sequences is determined by a Needelman-Wunsch alignment, useful for both protein and DNA alignments. For protein alignments the default scoring matrix used is BLOSUM50, and the penalty for the first residue in a gap is −12, while the penalty for additional residues in a gap is −2. The alignment may be made with the Align software from the FASTA package version v20u6 (W. R. Pearson and D. J. Lipman (1988), "Improved Tools for Biological Sequence Analysis", PNAS 85:2444-2448; and W. R. Pearson (1990) "Rapid and Sensitive Sequence Comparison with FASTP and FASTA", Methods in Enzymology, 183:63-98).

Non-limiting examples of IL-21 variants having substantially modified biological activity relative to wild-type IL-21 is described in WO03/40313 wherein substitutions of single amino acids in the IL-21 sequence antagonises the effect of IL-21.

According to this invention antagonists of IL-21 compounds which inhibit the activity normally observed with IL-21. Such compounds may be as well small molecules, peptides or soluble receptors interacting with IL-21. According to the present invention derivatisation of the antagonists of IL-21 are peptides or soluble receptors. In an aspect of the invention the peptides are IL-21 analogues or variants having an antagonistic effect.

Antagonists are also fusion protein that includes the extracellular domain of the IL-21 R fused to an Fc immunoglobulin region, Examples of antagonistic fusion proteins are shown in SEQ ID NO:23 (SEQ ID NO:3 of this disclosure), SEQ ID NO:25 (SEQ ID NO:4 of this disclosure), SEQ ID NO:27 (SEQ ID NO:5 of this disclosure), SEQ ID NO:29 (SEQ ID NO:6 of this disclosure), SEQ ID NO:31 (SEQ ID NO:7 of this disclosure), SEQ ID NO:33 (SEQ ID NO:8 of this disclosure), SEQ ID NO:35 (SEQ ID NO:9 of this disclosure), SEQ ID NO:37 (SEQ ID NO:10 of this disclosure), or SEQ ID NO:39, of WO03/28630 (SEQ ID NO:11 of this disclosure).

Other IL-21 antagonists to be used according to the invention are the sequences 4 and 6 of WO03/40313 (SEQ ID NOS: 12 and 13 of this disclosure). The IL-21 peptides with variations in one or both of the positions 114 and 119 as mentioned in WO03/87320.

Soluble receptors of IL-21 having antagonistic effect on IL-21 are disclosed in WO04/07682.

Examples of antagonistic fusion proteins that can be used in the methods of the invention are shown in SEQ ID NO:23 (SEQ ID NO:3 of this disclosure), SEQ ID NO:25 (SEQ ID NO:4 of this disclosure), SEQ ID NO:27 (SEQ ID NO:5 of this disclosure), SEQ ID NO:29 (SEQ ID NO:6 of this disclosure), SEQ ID NO:31 (SEQ ID NO:7 of this disclosure), SEQ ID NO:33 (SEQ ID NO:8 of this disclosure), SEQ ID NO:35 (SEQ ID NO:9 of this disclosure), SEQ ID NO:37 (SEQ ID NO:10of this disclosure), and SEQ ID NO:39, of WO03/28630 (SEQ ID NO:11 of this disclosure).

Other IL-21 antagonists that can be used in inventive methods provided here are SEQ ID NOS 4 and 6 of WO03/40313 (SEQ ID NOS: 12 and 13 of this disclosure) and IL-21 peptides with variations in one or both of the positions 114 and 119 of human IL-21 as mentioned in WO03/87320. WO04/07682 describes soluble receptors having antagonistic activity against IL-21.

In an aspect of the invention, IL-21 antibodies are used as IL-21 antagonists. Such antibodies can be produced by any suitable method known in the art and examples of such antibodies are described in WO00/53761. IL-21 antagonist antibodies are characterised by inhibiting one or more biological activities of IL-21. Inhibition of biologic activity can be measured by, e.g., the Ba F3 assay where Ba F3 cells stably transfected with human IL-21 R (IL-21R-Ba F3) undergo proliferation when IL-21 is added to the culture. Addition of IL-21 antagonists to the IL-21R-Ba F3 cells desirably partially or fully inhibits IL-21-dependent proliferation of IL-21R-Ba F3 cells.

The term "polymeric molecule", or "polymeric group" or "polymeric moiety" or "polymer molecule", encompasses molecules formed by covalent linkage of two or more monomers wherein none of the monomers is an amino acid residue. Preferred polymers are polymer molecules selected from the group consisting of dendrimers as disclosed in PCT/DK2004/000531, polyalkylene oxide (PAO), including polyalkylene glycol (PAG), such as polyethylene glycol (PEG) and polypropylene glycol (PPG), branched PEGs, polyvinyl alcohol (PVA), polycarboxylate, poly-vinylpyrrolidone, polyethylene-co-maleic acid anhydride, polystyrene-co-maleic acid anhydride, and dextran, including carboxymethyl-dextran, PEG being particularly preferred.

The term "PEGylated IL-21" means IL-21, having one or more PEG molecule conjugated to a human IL-21 polypeptide. It is to be understood, that the PEG molecule may be attached to any part of the IL-21 polypeptide including any amino acid residue or carbohydrate moiety of the IL-21 polypeptide. The term "cysteine-PEGylated IL-21" means IL-21 having a PEG molecule conjugated to a sulfhydryl group of a cysteine introduced in IL-21.

The term "polyethylene glycol" or "PEG" means a polyethylene glycol compound or a derivative thereof, with or without coupling agents, coupling or activating moeities (e.g., with thiol, triflate, tresylate, aziridine, oxirane, or preferably with a maleimide moiety). Compounds such as maleimido monomethoxy PEG are exemplary of activated PEG compounds of the invention. The term "PEG" is intended to indicate polyethylene glycol of a molecular weight between 500 and 150,000 Da, including analogues thereof, wherein for instance the terminal OH-group has been replaced by a methoxy group (referred to as mPEG).

In the present context, the words "peptide" and "polypeptide" and "protein" are used interchangeably and are intended to indicate the same.

In the context of the present invention "treatment" or "treating" refers to preventing, alleviating, managing, curing or reducing the disease e.g. a symptom of the disease, a condition underlying the disease or both.

The term "functional in vivo half-life" is used in its normal meaning, i.e., the time at which 50% of the biological activity of the polypeptide or conjugate is still present in the body/target organ, or the time at which the activity of the polypeptide or conjugate is 50% of its initial value. As an alternative to determining functional in vivo half-life, "serum half-life" may be determined, i.e., the time at which 50% of the polypeptide or conjugate molecules circulate in the plasma or bloodstream prior to being cleared. Determination of serum-half-life is often more simple than determining functional half-life and the magnitude of serum-half-life is usually a good indication of the magnitude of functional in vivo half-life. Alternative terms to serum half-life include plasma half-life, circulating half-life, circulatory half-life, serum clearance, plasma clearance, and clearance half-life. The functionality to be retained is normally selected from procoagulant, proteolytic, co-factor binding, receptor binding activity, or other type of biological activity associated with the particular protein.

The term "increased" with respect to the functional in vivo half-life or plasma half-life is used to indicate that the relevant half-life of the polypeptide or conjugate is statistically significantly increased relative to that of a reference molecule, such as non-conjugated glycoprotein as determined under comparable conditions. For instance the relevant half-life may be increased by at least about 25%, such as by at least about 50%, e.g., by at least about 100%, 150%, 200%, 250%, or 500%.

In one embodiment the present invention relates to a use of a derivative of IL-21 for the preparation of a medicament for the treatment of diseases responsive to stimulation of T cell and NK cell proliferation.

The present invention further provides a variety of other polypeptide fusions [and related multimeric proteins comprising one or more polypeptide fusions]. For example, a IL-21 polypeptide can be prepared as a fusion to a dimerizing protein as disclosed in U.S. Pat. Nos. 5,155,027 and 5,567,584 and derivatised according to the invention. Preferred dimerizing proteins in this regard include immunoglobulin constant region domains. Immunoglobulin-IL-21 polypeptide fusions can be expressed in genetically engineered cells. Auxiliary domains can be fused to IL-21 polypeptides to target them to specific cells, tissues, or macromolecules (e.g., collagen).

The peptides of the present invention, including full-length peptides, peptide fragments (e.g. ligand-binding fragments), and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: A Laboratory Manual, 2nd ed. (Cold Spring Harbor Laboratory Press, Cold Spring Harbor, N.Y., 1989), and Ausubel et al., ibid.

It is to be recognized that according to the present invention, when a cDNA is claimed as described above, it is understood that what is claimed are both the sense strand, the anti-sense strand, and the DNA as double-stranded having both the sense and anti-sense strand annealed together by their respective hydrogen bonds. Also claimed is the messenger RNA (mRNA) which encodes the polypeptides of the present invention, and which mRNA is encoded by the above-described cDNA. A messenger RNA (mRNA) will encode a polypeptide using the same codons as those defined above, with the exception that each thymine nucleotide (T) is replaced by a uracil nucleotide (U).

To direct an IL-21 polypeptide into the secretory pathway of a host cell, a secretory signal sequence (also known as a leader sequence, prepro sequence or pre sequence) is provided in the expression vector. The secretory signal sequence may be that of the protein, or may be derived from another secreted protein (e.g.,) or synthesized de novo. The secretory signal sequence is joined to the IL-21 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

IL-21 and variants thereof may be expressed in E-coli as described in WO 04/55168. Optionally IL-21 variants may be produced by recombinant DNA techniques in other organisms. To this end, DNA sequences encoding human IL-21 related polypeptides or IL-21 variants may be isolated by preparing a genomic or cDNA library and screening for DNA sequences coding for all or part of the protein by hybridization using synthetic oligonucleotide probes in accordance with standard techniques (cf. Sambrook et al., *Molecular Cloning: A Laboratory Manual*, Cold Spring Harbor Laboratory, Cold Spring Harbor, N.Y., 1989). For the present purpose, the DNA sequence encoding the protein is preferably of human origin, i.e. derived from a human genomic DNA or cDNA library.

The DNA sequences encoding the IL-21 variants may also be prepared synthetically by established standard methods, e.g. the phosphoramidite method described by Beaucage and Caruthers, *Tetrahedron Letters* 22 (1981), 1859-1869, or the method described by Matthes et al., *EMBO Journal* 3 (1984), 801-805. According to the phosphoramidite method, oligonucleotides are synthesized, e.g. in an automatic DNA synthesizer, purified, annealed, ligated and cloned in suitable vectors.

The invention also comprises chemical modifications of the IL-21 polypeptide, variant thereof or fusion proteins comprising IL-21 or variants thereof. The chemical modification comprises covalent modifications with an organic agent capable of reacting with a selected side chain or a terminal residue.

Examples of such modifications are wherein a lipophilic substituent is attached to one or more amino acid residues at a position relative to the amino acid sequence of SEQ ID NO:1 or 2 of WO00/53761 (SEQ ID NO:2 of this disclosure) as described above. It is to be understood that an amino acid residues at the position relative to the amino acid sequence of SEQ ID NO:2 (SEQ ID NO:2 of this disclosure) may be any amino acid residue and not only the amino acid residue naturally present at that position. In one embodiment the lipophilic substituent is attached to a lysine.

One or more of the lysines in IL-21 could be derivatives as described in the application. In other preferred embodiments, additional lysines are substituted, inserted into the sequence or added at the N-terminal or C-terminal, and then optionally derivatised. Other aspects of the invention includes addition of asp, glu, cys, gln, ser, thr, or tyr which carries function groups in the side chain for derivatising.

Preferred regions of insertions are where the overall activity of the protein is not adversely affected. N-terminal and C-terminal truncations may occur simultaneously as well as additions in the terminal of appropriate sequences.

In aspects of the invention any of the following positions are selected for substitution optionally in combination: Lys22, Lys53, Lys57, Lys76, Lys78, Lys89, Lys102, Lys103, Lys106, Lys113 or Lys118.

In an aspect of the invention the following substituents may be derivatised, optionally in combination and optionally after preparing variants with Lysine in the corresponding positions; Arg66, Arg86, Arg87, Arg91, Arg111 or Arg127. All of the above positions are calculated from the positions of the IL-21 peptide as described in WO0/53761 without the initial N-terminal sequence of 28 amino acids.

The term "lipophilic substituent" is characterised by comprising 4-40 carbon atoms and having a solubility in water at 20° C. in the range from about 0.1 mg/100 ml water to about 250 mg/100 ml water, such as in the range from about 0.3 mg/100 ml water to about 75 mg/100 ml water. For instance, octanoic acid (C8) has a solubility in water at 20° C. of 68 mg/100 ml, decanoic acid (C10) has a solubility in water at 20° C. of 15 mg/100 ml, and octadecanoic acid (C18) has a solubility in water at 20° C. of 0.3 mg/100 ml.

To obtain a satisfactory protracted profile of action of the IL-21 derivative, the lipophilic substituent attached to the IL-21 moiety, as an example comprises 4-40 carbon atoms, such as 8-25 carbon atoms. The lipophilic substituent may be attached to an amino group of the IL-21 moiety by means of a carboxyl group of the lipophilic substituent which forms an amide bond with an amino group of the amino acid to which it is attached. As an alternative, the lipophilic substituent may be attached to said amino acid in such a way that an amino group of the lipophilic substituent forms an amide bond with a carboxyl group of the amino acid. As a further option, the lipophililic substituent may be linked to the IL-21 moiety via an ester bond. Formally, the ester can be formed either by reaction between a carboxyl group of the IL-21 moiety and a hydroxyl group of the substituent-to-be or by reaction between a hydroxyl group of the IL-21 moiety and a carboxyl group of the substituent-to-be. As a further alternative, the lipophilic substituent can be an alkyl group which is introduced into a primary amino group of the IL-21 moiety In one embodiment of the invention the IL-21 derivative only has one lipophilic substituent attached to the IL-21 peptide.

In one embodiment of the invention the lipophilic substituent comprises from 4 to 40 carbon atoms.

In one embodiment of the invention the lipophilic substituent comprises from 8 to 25 carbon atoms.

In one embodiment of the invention the lipophilic substituent comprises from 12 to 20 carbon atoms.

In one embodiment of the invention the lipophilic substituent is attached to an amino acid residue in such a way that a carboxyl group of the lipophilic substituent forms an amide bond with an amino group of the amino acid residue.

In other preferred embodiments, additional lysines are substituted, inserted into the sequence or added at the N-terminal or C-terminal, and then optionally derivatised.

Preferred regions of insertions are where the overall activity of the protein is not adversely affected. Preferred regions are the positions listed above.

In one embodiment of the invention the lipophilic substituent is attached to an amino acid residue in such a way that an amino group of the lipophilic substituent forms an amide bond with a carboxyl group of the amino acid residue.

In one embodiment of the invention the lipophilic substituent is attached to the IL-21 peptide by means of a spacer.

In one embodiment of the invention the spacer is an unbranched alkane α,ω-dicarboxylic acid group having from 1 to 7 methylene groups, such as two methylene groups which spacer forms a bridge between an amino group of the IL-21 peptide and an amino group of the lipophilic substituent.

In one embodiment of the invention the spacer is an amino acid residue except a Cys residue, or a dipeptide. Examples of suitable spacers includes β-alanine, gamma-aminobutyric acid (GABA), γ-glutamic acid, succinic acid, Lys, Glu or Asp, or a dipeptide such as Gly-Lys. When the spacer is succinic acid, one carboxyl group thereof may form an amide bond with an amino group of the amino acid residue, and the other carboxyl group thereof may form an amide bond with an amino group of the lipophilic substituent. When the spacer is Lys, Glu or Asp, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the ε-amino group of Lys and the lipophilic substituent. In one embodiment, such a further spacer is succinic acid which forms an amide bond with the ε-amino group of Lys and with an amino group present in the lipophilic substituent. In another embodiment such a further spacer is Glu or Asp which forms an amide bond with the ε-amino group of Lys and another amide bond with a carboxyl group present in the lipophilic substituent, that is, the lipophilic substituent is a $N^\epsilon$-acylated lysine residue.

In one embodiment of the invention the spacer is selected from the list consisting of β-alanine, gamma-aminobutyric acid (GABA), γ-glutamic acid, Lys, Asp, Glu, a dipeptide containing Asp, a dipeptide containing Glu, or a dipeptide containing Lys. In one embodiment of the invention the spacer is β-alanine. In one embodiment of the invention the spacer is gamma-aminobutyric acid (GABA). In one embodiment of the invention the spacer is γ-glutamic acid.

In one embodiment of the invention a carboxyl group of the parent IL-21 peptide forms an amide bond with an amino group of a spacer, and the carboxyl group of the amino acid or dipeptide spacer forms an amide bond with an amino group of the lipophilic substituent.

In one embodiment of the invention an amino group of the parent IL-21 peptide forms an amide bond with a carboxylic group of a spacer, and an amino group of the spacer forms an amide bond with a carboxyl group of the lipophilic substituent.

In one embodiment of the invention the lipophilic substituent comprises a partially or completely hydrogenated cyclopentanophenathrene skeleton.

In one embodiment of the invention the lipophilic substituent is an straight-chain or branched alkyl group. In one embodiment of the invention the lipophilic substituent is the acyl group of a straight-chain or branched fatty acid.

In one embodiment of the invention the acyl group of a lipophilic substituent is selected from the group comprising $CH_3(CH_2)_nCO-$, wherein n is 4 to 38, such as $CH_3(CH_2)_6$ $CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$.

In one embodiment of the invention the lipophilic substituent is an acyl group of a straight-chain or branched alkane α,ω-dicarboxylic acid.

In one embodiment of the invention the acyl group of the lipophilic substituent is selected from the group comprising $HOOC(CH_2)_mCO-$, wherein m is 4 to 38, such as $HOOC(CH_2)_{14}CO-$, $HOOC(CH_2)_{16}CO-$, $HOOC(CH_2)_{18}CO-$, $HOOC(CH_2)_{20}CO-$ and $HOOC(CH_2)_{22}CO-$.

In one embodiment of the invention the lipophilic substituent is a group of the formula $CH_3(CH_2)_p((CH_2)_qCOOH)CHNH-CO(CH_2)_2CO-$, wherein p and q are integers and p+q is an integer of from 8 to 40, such as from 12 to 35.

In one embodiment of the invention the lipophilic substituent is a group of the formula $CH_3(CH_2)_rCO-NHCH(COOH)(CH_2)_2CO-$, wherein r is an integer of from 10 to 24.

In one embodiment of the invention the lipophilic substituent is a group of the formula $CH_3(CH_2)_sCO-NHCH((CH_2)_2COOH)CO-$, wherein s is an integer of from 8 to 24.

In one embodiment of the invention the lipophilic substituent is a group of the formula $COOH(CH_2)_tCO-$ wherein t is an integer of from 8 to 24.

In one embodiment of the invention the lipophilic substituent is a group of the formula $-NHCH(COOH)(CH_2)_4NH-CO(CH_2)_uCH_3$, wherein u is an integer of from 8 to 18.

In one embodiment of the invention the lipophilic substituent is a group of the formula $-NHCH(COOH)(CH_2)_4NH-COCH((CH_2)_2COOH)NH-CO(CH_2)_wCH_3$, wherein w is an integer of from 10 to 16.

In one embodiment of the invention the lipophilic substituent is a group of the formula $-NHCH(COOH)(CH_2)_4NH-CO(CH_2)_2CH(COOH)NH-CO(CH_2)_xCH_3$, wherein x is an integer of from 10 to 16.

In one embodiment of the invention the lipophilic substituent is a group of the formula $-NHCH(COOH)(CH_2)_4NH-CO(CH_2)_2CH(COOH)NHCO(CH_2)_yCH_3$, wherein y is zero or an integer of from 1 to 22.

In one embodiment of the invention the lipophilic substituent is N-Lithocholoyl.

In one embodiment of the invention the lipophilic substituent is N-Choloyl.

In one embodiment of the invention the IL-21 derivative has one lipophilic substituent. In one embodiment of the invention the IL-21 derivative has two lipophilic substituents. In one embodiment of the invention the IL-21 derivative has three lipophilic substituents. In one embodiment of the invention the IL-21 derivative has four lipophilic substituents.

The methods of the present invention also contemplate using chemically modified IL-21 compositions, in which an IL-21 polypeptide is linked with a polymeric molecule. Illustrative IL-21 polypeptides are soluble polypeptides that lack a functional transmembrane domain, such as a mature IL-21 polypeptide. Typically, the polymer is water soluble so that the IL-21 conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce IL-21 conjugates. IL-21 conjugates used for therapy can comprise pharmaceutically acceptable water-soluble polymer moieties. Suitable water-soluble polymers include polyethylene glycol (PEG), monomethoxy- PEG, mono-(C1-C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Different sizes of PEG are described above.

In an aspect of the invention the peptide is derivatised with a N-terminal PEG group by oxidation of a serine with sodium periodate, followed by reaction of PEG-derivative, to which a hydroxylamine was attached, yielding an oxime. In principle, the serine could also have been an internal serine residue or an added serine residue as described above.

Other methods for attaching PEG groups are described in G. Pasut, A. Guiotto, F. M. Veronese *Expert Opin. Ther. Patents* 2004, 14, 859-894. Variants of IL-21 suitable for attachment of polymeric groups may be obtained as described above.

In an aspect of the invention IL-21 is attached in the C-terminal of the peptide. This may be achieved by using IL-21 or a variant of IL-21 suitable as a substrate for CPY (carboxypeptidase Y) of which part of the reaction is described in in EP243929. This intermediate may then be further substituted by a compound containing one or more reactive groups, X, suitable for further substitution of with molecules containing the reactive group Y. The reactive group may be selected from the groups mentioned below.

In one embodiment the functional groups of X and Y are selected from amongst carbonyl groups, such as keto and aldehyde groups, and amino derivatives, such as

| | |
|---|---|
| hydrazine derivatives | —NH—NH$_2$, |
| hydrazine carboxylate derivatives | —O—C(O)—NH—NH$_2$, |
| semicarbazide derivatives | —NH—C(O)—NH—NH$_2$, |
| thiosemicarbazide derivatives | —NH—C(S)—NH—NH$_2$, |
| carbonic acid dihydrazide derivatives | —NHC(O)—NH—NH—C(O)—NH—NH$_2$, |
| carbazide derivatives | —NH—NH—C(O)—NH—NH$_2$, |
| thiocarbazide derivatives | —NH—NH—C(S)—NH—NH$_2$, |
| aryl hydrazine derivatives | —NH—C(O)—C$_6$H$_4$—NH—NH$_2$, and |
| hydrazide derivatives | —C(O)—NH—NH$_2$; |
| oxylamine derivatives, such as | —O—NH$_2$, —C(O)—O—NH$_2$, —NH—C(O)—O—NH$_2$ and —NH—C(S)—O—NH$_2$. |

It is to be understood, that if the functional group comprised in X is a carbonyl group, then the functional group comprised in Y is an amine derivative, and vice versa. Due to the presence of —NH$_2$ groups in most peptides, a better selectivity is believed to be obtained if X comprises a keto- or an aldehyde-functionality.

Examples of derivatives of PEG suitable in the reaction described above are

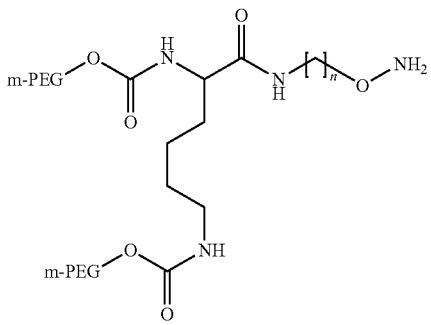

wherein n is 1, 2, 3, 4, 5 or 6 and mPEG has a molecular weight of 10 kDa, 20 kDa, 30 kDa or 40 kDa.

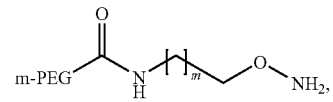

wherein m is 1, 2, 3, 4, 5 or 6 and mPEG has a molecular weight of 10 kDa, 20 kDa, 30 kDa or 40 kDa.

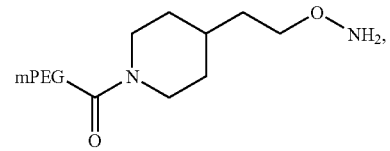

wherein mPEG has a molecular weight of 10 kDa, 20 kDa, 30 kDa or 40 kDa,

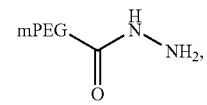

wherein mPEG has a molecular weight of 10 kDa, 20 kDa, 30 kDa or 40 kDa,

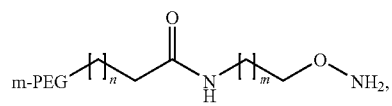

wherein n is 0, 1, 2, 3, 4, 5 or 6 and m is 1, 2, 3, 4, 5 or 6 and mPEG has a molecular weight of 10 kDa, 20 kDa, 30 kDa or 40 kDa,

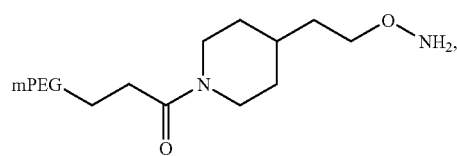

wherein mPEG has a molecular weight of 10 kDa, 20 kDa, 30 kDa or 40 kDa,

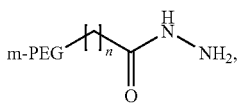

wherein n is 1, 2, 3, 4, 5 or 6 and mPEG has a molecular weight of 10 kDa, 20 kDa, 30 kDa or 40 kDa,

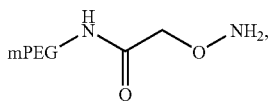

wherein mPEG has a molecular weight of 10 kDa, 20 kDa, 30 kDa or 40 kDa,

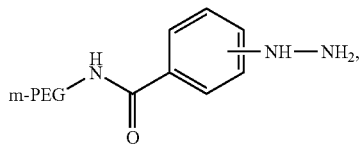

wherein mPEG has a molecular weight of 10 kDa, 20 kDa, 30 kDa or 40 kDa,

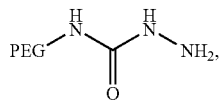

wherein mPEG has a molecular weight of 10 kDa, 20 kDa, 30 kDa or 40 kDa,

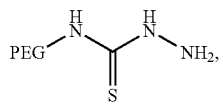

wherein mPEG has a molecular weight of 10 kDa, 20 kDa, 30 kDa or 40 kDa,

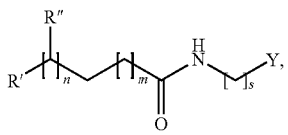

wherein Y is —O—NH$_2$, NH—NH$_2$, n, m and s are any number from 0 to 20;

R' and R" independently represents for example methyl, phenyl, biphenyl, phenoxyphenyl, phenylcarboxyphenyl.

At any suitable position in the alkyl chains in any of the formulas above a group of the formula —SO$_2$—, —C(O)NH—, —C(O)NHSO$_2$—, —SO$_2$-phenyl-, C(O)NHSO$_2$-phenyl- may be inserted in either direction. Optionally the group C(O)NH in the above formula may be substituted by

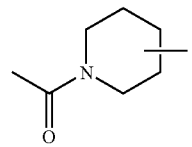

In an embodiment of the invention the introduction of the derivative is introduced in one step. The R—X then contains the derivatives to be introduced into IL-21. The nucleophile represents for example amino acids, which have been modified to carry the derivative. In principle any sequence of amino acids may be used. In an aspect of the invention nucleophiles such as G$_{(1-5)}$-PEG (SEQ ID NO:18), G$_{(1-5)}$-lipid (SEQ ID NO:19), G$_{(1-4)}$-NH—CH$_2$—CHO (SEQ ID NO:20), G$_{(1-4)}$-NH—CH$_2$C—O—NH$_2$ (SEQ ID NO:21), etc. are used.

PEG is a suitable polymer molecule, since it has only few reactive groups capable of cross-linking compared to polysaccharides such as dextran. In particular, monofunctional PEG, e.g. methoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule are provided in activated form, i.e. with reactive functional groups. Suitable activated polymer molecules are commercially available, e.g. from Shearwater Corp., Huntsville, Ala., USA, or from PolyMASC Pharmaceuticals plc, UK. Alternatively, the polymer molecules can be activated by conventional methods known in the art, e.g. as disclosed in WO 90/13540. Specific examples of activated linear or branched polymer molecules for use in the present invention are described in the Shearwater Corp. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG), BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. Nos. 5,932,462 and 5,643,575, both of which are incorporated herein by reference. Furthermore, the following publications, incorporated herein by reference, disclose useful polymer molecules and/or PEGylation chemistries: U.S. Pat. Nos. 5,824,778, 5,476,653, WO 97/32607, EP 229,108, EP 402,378, U.S. Pat. Nos. 4,902,502, 5,281,698, 5,122,614, 5,219,564, WO 92/16555, WO 94/04193, WO 94/14758, WO 94/17039, WO 94/18247, WO 94/28024, WO 95/00162, WO 95/11924, WO 95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. Nos. 5,473,034, 5,516,673, EP 605 963, U.S. Pat. No. 5,382,657, EP 510 356, EP 400 472, EP 183 503 and EP 154 316.

The conjugation of the polypeptide and the activated polymer molecules is conducted by use of any conventional method, e.g. as described in the following references (which also describe suitable methods for activation of polymer molecules): R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). The skilled person will be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfydryl, succinimidyl, maleimide, vinysulfone or haloacetate). The PEG-ylation may be directed towards conjugation to all available attachment groups on the polypeptide (i.e. such attachment groups that are exposed at the surface of the polypeptide) or may be directed towards one or more specific attachment groups, e.g. the N-terminal amino group (U.S. Pat. No. 5,985,265). Furthermore, the conjugation may be achieved in one step or in a stepwise manner (e.g. as described in WO 99/55377).

It will be understood that the PEGylation is designed so as to produce the optimal molecule with respect to the number of PEG molecules attached, the size and form of such molecules (e.g. whether they are linear or branched), and where in the polypeptide such molecules are attached. The molecular weight of the polymer to be used will be chosen taking into consideration the desired effect to be achieved. For instance, if the primary purpose of the conjugation is to achieve a conjugate having a high molecular weight and larger size (e.g. to reduce renal clearance), one may choose to conjugate either one or a few high molecular weight polymer molecules or a number of polymer molecules with a smaller molecular weight to obtain the desired effect. Preferably, however, several polymer molecules with a lower molecular weight will be used. This is also the case if a high degree of epitope shielding is desired. In such cases, 2-8 polymers with a molecular weight of e.g. about 5,000 Da, such as 3-6 such polymers, may for example be used. As the examples below illustrate, it may be advantageous to have a larger number of polymer molecules with a lower molecular weight (e.g. 4-6 with a MW of 5000) compared to a smaller number of polymer molecules with a higher molecular weight (e.g. 1-3 with a MW of 12,000-20,000) in terms of improving the functional in vivo half-life of the polypeptide conjugate, even where the total molecular weight of the attached polymer molecules in the two cases is the same or similar. It is believed that the presence of a larger number of smaller polymer molecules provides the polypeptide with a larger diameter or apparent size than e.g. a single yet larger polymer molecule, at least when the polymer molecules are relatively uniformly distributed on the polypeptide surface. It has further been found that advantageous results are obtained when the apparent size (also referred to as the "apparent molecular weight" or "apparent mass") of at least a major portion of the conjugate of the invention is at least about 50 kDa, such as at least about 55 kDa, such as at least about 60 kDa, e.g. at least about 66 kDa. This is believed to be due to the fact that renal clearance is substantially eliminated for conjugates having a sufficiently large apparent size. In the present context, the "apparent size" of a IL-21 conjugate or IL-21 polypeptide is determined by the SDS-PAGE method.

In an embodiment of the invention PEG is conjugated to a peptide according to the present invention may be of any molecular weight. In particular the molecular weight may be between 500 and 100,000 Da, such as between 500 and 60,000 Da, such as between 1000 and 40,000 Da, such as between 5,000 and 40,000 Da. In particular, PEG with molecular weights of 10,000 Da, 20,000 Da or 40,000 KDa may be used in the present invention. In all cases the PEGs may be linear or branched. In an embodiment of the invention the PEG groups are 5 kDa, 10 kDa, 20 kDa, 30 kDa, 40 kDa og 60 kDa.

In an embodiment of the invention, one or more polymeric molecules are added to the peptide.

The present invention provides compounds which are suitable for attachment of a polymeric group. In an embodiment of the invention the derivative thus provides a peptide which has an improved in vivo half life. This may be achieved by protecting the compound against chemical degradation, proteolytic degradation, or antibody recognition—or any other mechanism.

In an embodiment the compounds provided are less toxic.

In an embodiment the compounds provided are more water soluble

In an embodiment the compounds provided has a modified biodistribution.

The above are with reference to the non-derivatised analogues or to the hIL-21.

Pharmaceutical Compositions

The invention provides in a particular embodiment the following:

Another object of the present invention is to provide a pharmaceutical formulation comprising IL-21, analogues or derivatives thereof, or optionally together with any other compound mentioned in the present application which is present in a concentration from 0.1 mg/ml to 100 mg/ml, and wherein said formulation has a pH from 2.0 to 10.0. The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of IL-21 or any other compound as mentioned above and a buffer, wherein said compound is present in a concentration from 0.1 mg/ml or as mentioned above, preferably from 0.5 mg/ml-50 mg/ml and wherein said formulation has a pH from about 2.0 to about 10.0. Preferred pH is from 3.0 to about 8.0. Particular preferred range is from 4.0-6.0, such as for example the ranges 4.0-4.5, 4.5-5.0, 5.0-5.5 and 5.5-6.0.

In another embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethane, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable antimicrobial preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomersal, bronopol, benzoic acid, imidurea, chlorohexidine, sodium dehydroacetate, chlorocresol, ethyl p-hydroxybenzoate, benzethonium chloride, chlorphenesin (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or DL isomer) of a particular amino acid (e.g. glycine, methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or DL isomer) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolized glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyranoside), sphingoglycolipids (eg. ceramides, gangliosides), dodecylphosphocholine, hen egg lysolecithin, fusidic acid derivatives- (e.g. sodium tauro-dihydrofusidate etc.), long-chain fatty acids and salts thereof C6-C12 (eg. oleic acid and caprylic acid), acylcarnitines and derivatives, $N^{\alpha}$-acylated derivatives of lysine, arginine or histidine, or side-chain acylated derivatives of lysine or arginine, $N^{\alpha}$-acylated derivatives of dipeptides comprising any combination of lysine, arginine or histidine and a neutral or acidic amino acid, $N^{\alpha}$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19th edition, 1995.

It is possible that other ingredients may be present in the peptide pharmaceutical formulation of the present invention.

Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing IL-21 or any other compound as mentioned above according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of IL-21 or any other compound as mentioned above, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of IL-21 or any other compound as mentioned above using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of IL-21 or any other compound as mentioned above, in the form of a nasal or pulmonal spray. As a still further option, the pharmaceutical compositions containing IL-21 or any other compound as mentioned above can also be adapted to transdermal administration, e.g. by needle-free injection or from a patch, optionally an iontophoretic patch, or transmucosal, e.g. buccal, administration.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physically unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradation pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahem. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

EXAMPLES

Recombinant Interleukin 21 (IL21) was expressed as inclusion bodies in *E. coli* as described in WO04/55168 with a N-terminal extension (Met-Ser-hIL21). The N-terminal Met residue is removed by the protease systems present in *E. coli*, leaving Ser-hIL21. The Glu-Ala-Glu amino acid sequence can be present or absent.

The protein was refolded and purified to 90-95% purity using conventional chromatographic methods.

The pure protein was subsequently N-terminally PEGylated via oxidation of the N-terminal serine by reaction with sodium periodate, followed by reaction of PEG-derivative, to which a hydroxylamine was attached, yielding an oxime.

Subsequent purification was done using gelfiltration or size exclusion chromatography (SEC).

In an proliferation assay as for example the BAF3 assay described below, the pegylated IL21 was equipotent with the unpegylated standard, indicating that the pegylation does not interfere with receptor binding, and that the reaction procedure are not harmful to the protein.

Preparatory Examples

A method for the attachment of a PEG-moiety to the C-terminus of a IL-21 derivative may be performed analogously to the attachment of chemical moieties to other peptides or proteins described above:

A PEG-moiety may be attached to the C-terminus of IL-21 or an IL-21 derivative such as e.g. hIL-21, by a two step method.

In the first step, a suitable IL-21-analogue such as e.g. (hIL-21-yl)alanine is subjected to a transpeptidation reaction catalyzed by carboxypeptidase Y (CPY) in the presence of a suitable nucleophile e.g. (S)-2-amino-3-(4-(propargyloxy)phenyl)propanoic acid in a suitable buffer such as a HEPES/TMEDA-buffer at a suitable pH such e.g. pH 7.5 or pH8 at a suitable temperature such as e.g. room temperature 30° C. or 35° C.

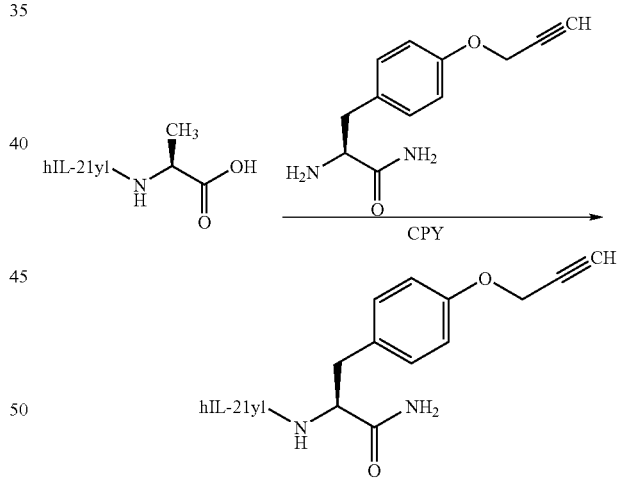

In the second step, a suitable derivatized PEG-reagent may be reacted with (S)-2-((hIL-21-yl)amino)-3-(4-(proparyloxy)phenyl)propanoic amide. E.g. an excess of 4-(mPEG20000-yl)-N-(3-(hydroxyimino)benzyl) butanoic amide may be reacted under oxidative conditions such as e.g. sodium hypochlorite solution to 4-(mPEG20000-yl)-N-(3-(oxycyano)benzylbutanoic amide. A solution of 4-(mPEG20000-yl)-N-(3-(oxycyano)benzylbutanoic amide may be added to a solution of (S)-2-((hIL-21-yl)amino)-3-(4-(proparyloxy)phenyl)propanoic amide to yield (S)-2-((hIL-21-yl)amino)-3-(4-((3-(3-((4-(mPEG20000-yl)butanoylamino)methyl)phenyl)isoxazol-5-yl)methoxy)phenyl)propanoic amide.

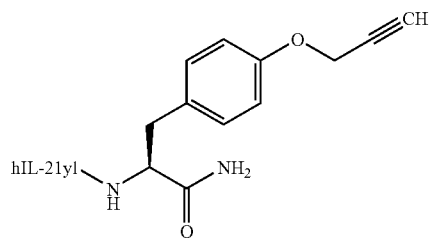
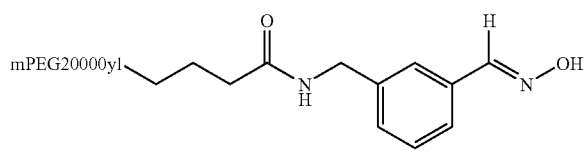
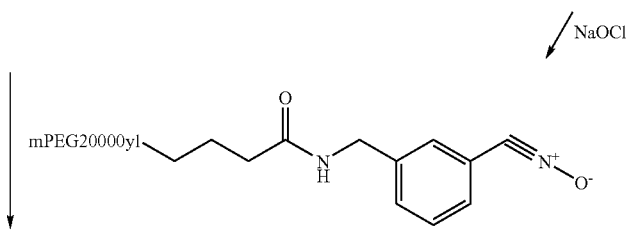
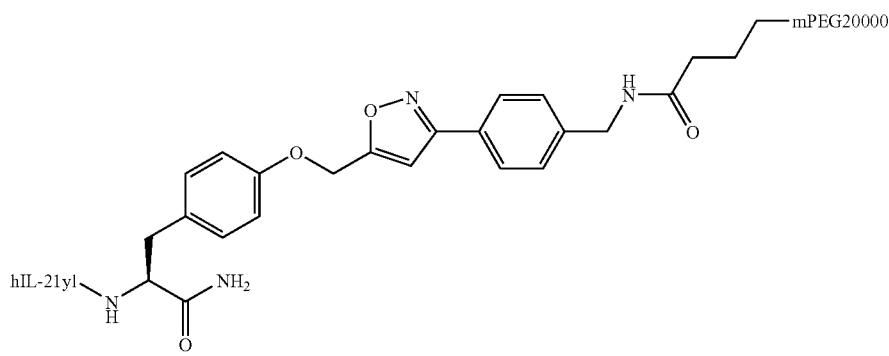

4-(mPEG20000-yl)-N-(3-(hydroxyimino)benzyl) butanoic amide may be prepared from commercially available 3-((tert-butoxycarbonylamino)methyl)benzoic acid, which may be reduced with a suitable reagent or combination of reagents e.g. in a two step procedure known to a person trained in the art, comprising in a first step addition of ethyl chloroformate in the presence of a base such as e.g. triethylamine, removal of the formed triethylammonium chloride by filtration and addition of lithium borohydride to yield tert-butyl N-(3-(hydroxylmethyl)benzyl)carbamate. tert-Butyl N-(3-(hydroxylmethyl)benzyl)carbamate may be oxidized with a suitable reagent or combination of reagents, e.g. using a Swern oxidation, known to a person trained in the art, comprising the addition of a solution of the alcohol in e.g. dichloromethane at −78° C. to a mixture of oxalyl chloride and dimethylsulfoxidein dichloromethane, which has been formed at −78° C., followed by addition of a suitable aminobase such as e.g. triethylamine and subsequent warming to room temperature. The formed tert-butyl N-(3-formylbenzyl) carbamate may be reacted to yield tert-butyl N-(3-((hydroxylimino)methyl)benzyl) by reaction with the free base or a suitable salt of hydroxylamine in a solution of e.g. sodium hydroxide in water. The BOC-protection group may be removed from tert-butyl N-(3-((hydroxylimino)methyl)benzyl) by methods described in the literature (e.g. T. W. Green, P. G. M Wuts Protective groups in organic synthesis $2^{nd}$ ed. Wiley, New York, 1991) e.g. by treatment with a 50% solution of trifluoroacetic acid in dichloromethane to give 3-(aminomethyl)benzaldehyde oxime. Finally, 4-(mPEG20000-yl)-N-(3-(hydroxyimino)benzyl) butanoic amide may be prepared by amide-forming reaction, comprising a reaction of the free base or a suitable salt of 3-(aminomethyl)benzaldehyde oxime in the presence of an excess of a suitable base such as e.g. ethyldiisopropylamine with commercially available 2,5-dioxypyrrolidinyl 4-(mPEG20000-yl)butanoic ester (Nektar, 2M450P01).

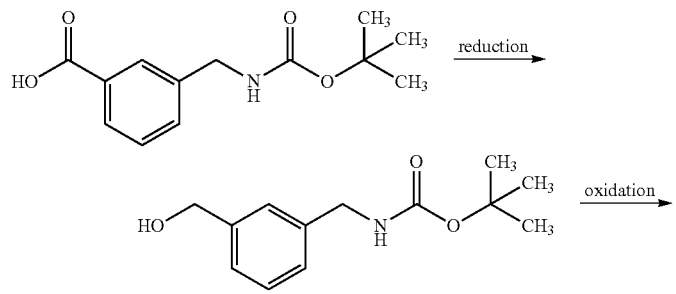

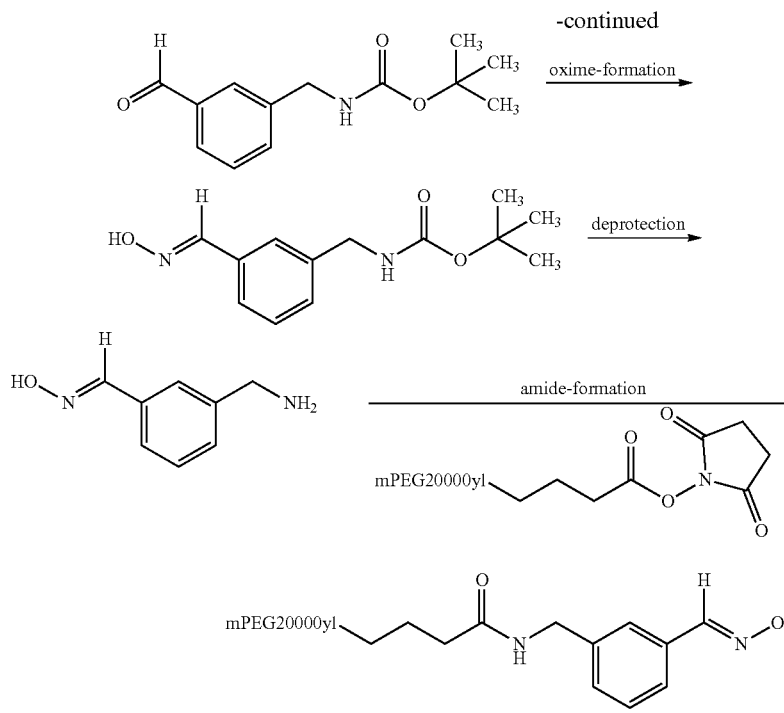

In an alternative second step, a mixture of an appropriate amount of copper sulphate pentahydrate, e.g. 5% or 10% or 1 equivalent or 10 equivalents with respect to (S)-2-((hIL-21-yl)amino)-3-(4-(proparyloxy)phenyl)propanoic amide and an appropriate amount of L-ascorbic acid, such as e.g. 50 eq with respect to (S)-2-((hIL-21-yl)amino)-3-(4-(proparyloxy) phenyl)propanoic amide, may be prepared in water, which is buffered with 2,6-lutidine. After a appropriate period of time such as e.g 5 min, this solution may be given to a solution of (S)-2-((hIL-21-yl)amino)-3-(4-(proparyloxy)phenyl)pro- panoic amide and N-(2-(mPEG20000-yl)ethyl) 11-azidoundecanoic amide which is buffered with 2,6-lutidine. The reaction mixture may be kept at a appropriate temperature such as e.g. room temperature until a mixture of a single compound selected from (S)-((hIL-21)amino)-3-(4-((1-(10-(N-(2-(mPEG20000-yl)ethyl)carbamoyl)decanyl)-1,2,3-triazol-4-yl)methoxy)phenyl) and (S)-((hIL-21)amino)-3-(4-((1-(10-(N-(2-(mPEG20000-yl)ethyl)carbamoyl)decanyl)-1,2,3-triazol-5-yl)methoxy)phenyl) and may be formed.

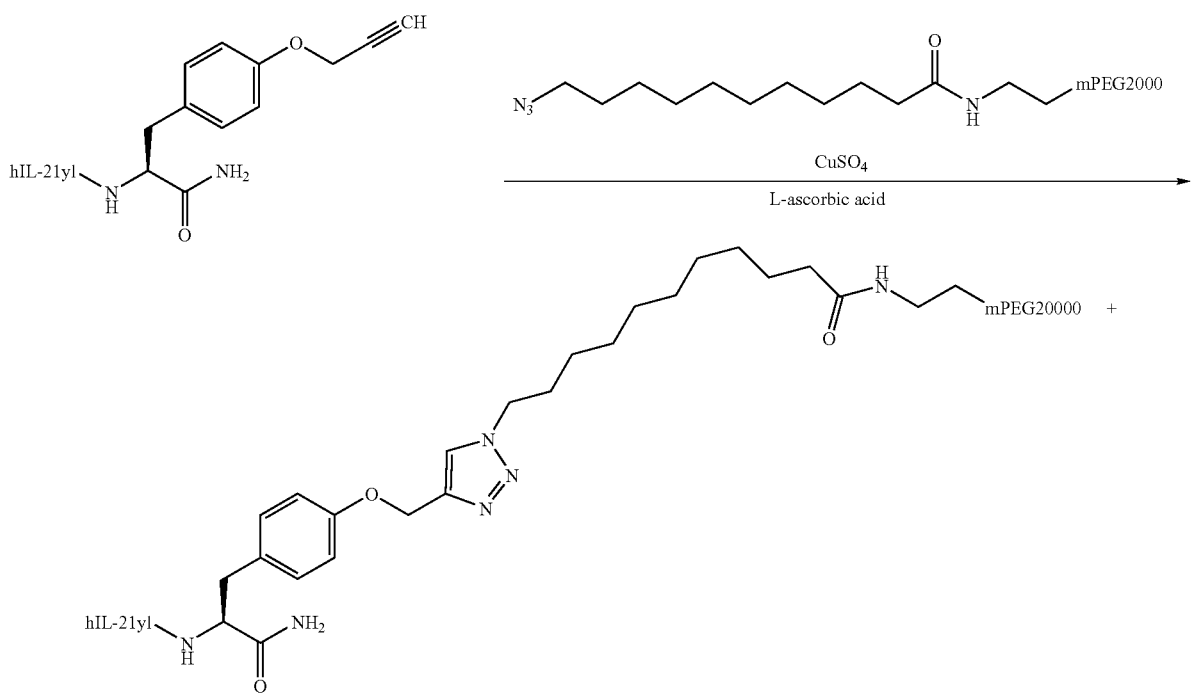

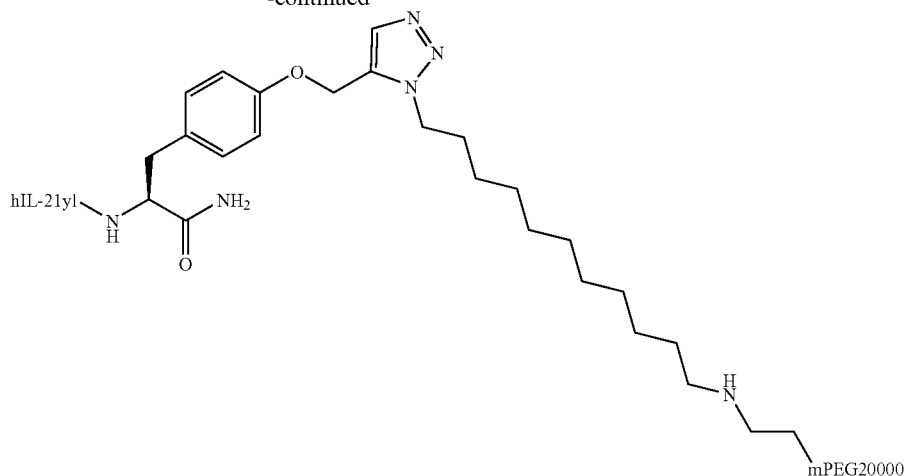

The synthesis of N-(2-(mPEG20000-yl)ethyl) 11-azidoundecanoic amide may be performed by reaction of commercially available methyl 11-bromoundecanoic ester with sodium azide in an appropriate solvent such as e.g. N,N-dimethylformamide at an appropriate temperature as e.g. 60° C. The formed methyl 11-azidoundecanoic ester may be saponified by a method known to a person skilled in the art and described in the literature (e.g. T. W. Green, P. G. M Wuts Protective groups in organic synthesis $2^{nd}$ ed. Wiley, New York, 1991) such as e.g. potassium hydroxide in methanol or potassium triethylsilanolate in tetrahydrofuran. The resulting acid may be activated by a method known to a person skilled in the art e.g. by reaction with 2-succinimido-1,1,3,3-tetramethyluronium tetrafluoroborate (TSTU) in an appropriate solvent such as e.g. N,N-dimethylformamide at an appropriate temperature such as e.g. room temperature to give 11-azido-N-2,5-dioxopyrrolidin-1-ylundecanoic amide. 11-Azido-N-2,5-dioxopyrrolidin-1-ylundecanoic amide may be reacted with commercially available (2-(mPEG20000-yl)ethyl)amine (Nektar 2M2U0P01) in an appropriate solvent such as e.g. dichloromethane and in the presence of an appropriate base such as e.g. triethylamine or ethyldiisopropylamine go give N-(2-(mPEG20000-yl)ethyl) 11-azidoundecanoic amide.

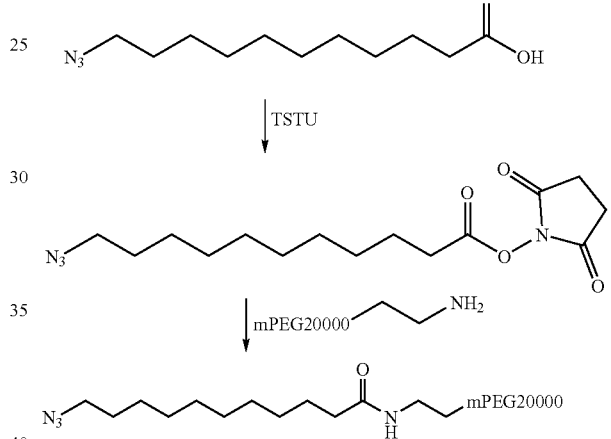

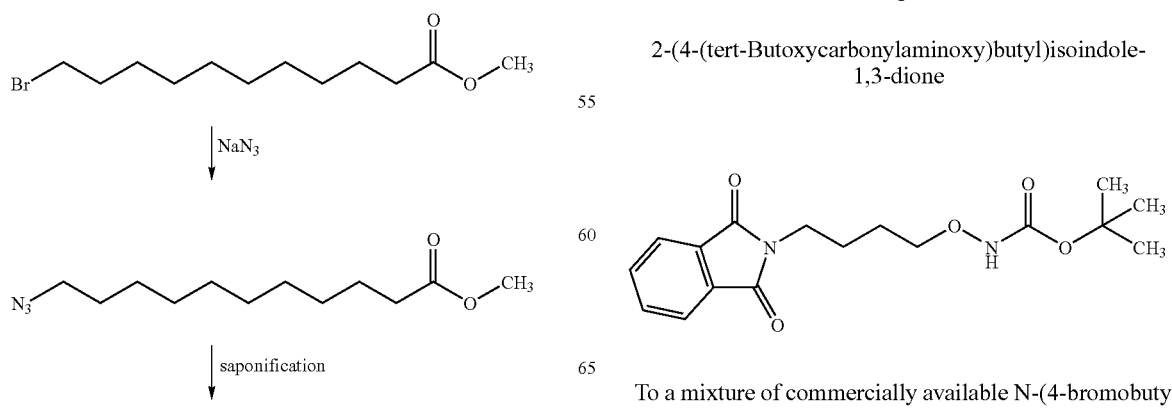

Example hIL-21 (SEQ ID NO:15) with N-terminal linker 1-(((((4-((4-(mPEG-20000-yl)butanoyl)amino)butox-iminoacetyl)serinyl)glutamyl)alaninyl)glutamyl) (SEQ ID NO:16), Step 1

2-(4-(tert-Butoxycarbonylaminoxy)butyl)isoindole-1,3-dione

To a mixture of commercially available N-(4-bromobutyl)phthalimide (2.82 g, 10 mmol) and N-Boc-hydroxylamine (2.08 g, 15.6 mmol) was added acetonitrile (2 ml) and successively 1,8-diazabicyclo[5.4.0]undec-7-ene (2.25 ml, 15 mmol). The reaction mixture was stirred at room temperature for 30 min and then at 50° C. for 2 days. It was diluted with a mixture of water (30 ml) and 1 N hydrochloric acid (20 ml). It was extracted with ethyl acetate (2×100 ml). The organic phase was washed with brine (50 ml) and was dried over magnesium sulphate. The crude product was purified by chromatography on silica (60 g), using a gradient of heptane/ethyl acetate 1:0 to 0:1 as eluent to give 2.08 g of 2-(4-(tert-butoxycarbonylaminoxy)butyl)isoindole-1,3-dione.

Step 2

N-(4-aminobutoxy)carbamic acid tert-butyl ester

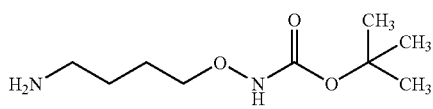

Hydrazine hydrate (1.0 ml, 20 mmol) was added to a solution of 2-(4-(tert-butoxycarbonylaminoxy)butyl)isoindole-1,3-dione (2.08 g, 6.22 mmol) in ethanol (8.0 ml). The reaction mixture was stirred at 80° C. for 65 h. The solvent was removed in vacuo. The residue was dissolved in toluene (10 ml) and the solvent was removed in vacuo. The residue was suspended in 1 N hydrochloric acid (10 ml). The precipitation was removed by filtration and was washed with water (2 ml). The filtrate and the wash-liquids were combined and made basic with potassium carbonate. The solution was extracted with dichloromethane (4×20 ml). The organic layer was dried over magnesium sulphate. The solvent was removed in vacuo to give 0.39 g of N-(4-aminobutoxy)carbamic acid tert-butyl ester. Potassium carbonate (3 g) was added to the aqueous phase, which was extracted with dichloromethane (3×20 ml). These combined organic layers were dried over magnesium sulphate. The solvent was removed in vacuo to give another 0.39 g of N-(4-aminobutoxy)carbamic acid tert-butyl ester.

Step 3

N-(4-(4-(mPEG20000-yl)butanolyamino)butoxy)carbamic acid tert-butyl ester

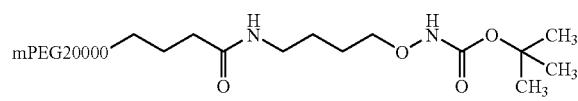

The commercially available N-hydroxysuccinimide ester of mPEG2000-ylbutanoic acid (Nektar "mPEG-SBA", # 2M450P01, 3 g, 0.15 mmol) was dissolved in dichloromethane (25 ml). N-(4-Aminobutoxy)carbamic acid tert-butyl ester (0.12 g, 0.59 mmol) was added. The reaction mixture was shaken at room temperature. Diethyl ether was added until a precipitation was obtained. The precipitation was isolated by filtration. The material was dried in vacuo to yield 2.39 g of N-(4-(4-(mPEG20000-yl)butanolyamino)butoxy)carbamic acid tert-butyl ester.

Step 4

N-(4-Aminoxybutyl)-4-(mPEG20000-yl)butanolyamide

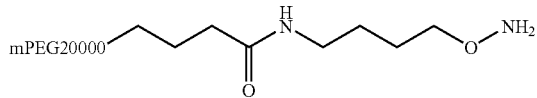

Trifluoroacetic acid (20 ml) was added to a solution of N-(4-(4-(mPEG20000-yl)butanolyamino)butoxy)carbamic acid tert-butyl ester (2.39 g, 0.12 mmol) in dichloromethane (20 ml). The reaction mixture was shaken for 30 min. Diethyl ether (100 ml) was added. The formed precipitation was isolated by filtration. It was washed with diethyl ether (2×100 ml) and dried in vacuo to give 1.96 g of N-(4-aminoxybutyl)-4-(mPEG20000-yl)butanolyamide Step 5 hIL-21 (SEQ ID NO:15) with N-terminal linker 1-(((((Serinyl)glutamyl)alninyl)glutamyl) (SEQ ID NO:16) (4 mg, lyophilized in a phosphate-buffer, 252 nmol) was dissolved in 0.400 ml of a buffer, consisting of triethanolamine (0.008 ml) in water (4 ml). A solution of methionine (3.15 mg, 21420 nmol) in water (0.12 ml) and a solution of sodium periodate (0.38 mg, 1890 nmol) were added successively. The reaction mixture was left for 30 min at room temperature. A solution of N-(4-aminoxybutyl)-4-(mPEG20000-yl)butanolyamide (77 mg, 3780 nmol) in water (0.240 ml) was added. The pH was adjusted to pH 4-5 with glacial acetic acid (0.004 ml). The reaction mixture was left at room temperature for 16 h. The reaction mixture was diluted with a solution of triethanolamine (12 mg) in water (3.2 ml) and was kept at −18° C. until purification.

Protein Chemistry

Human IL-21 sequences (hIL-21) without an N-terminal sequence, described and incorporated by reference from WO00/53761, are shown in SEQ ID NO:14 and SEQ ID NO:15, with and without a N-terminal Met, respectively. hIL-21 SEQ ID NO: 15) was expressed as inclusion bodies in E. coli with a N-terminal extension (Met-Ser-Glu-Ala-Glu SEQ ID NO:17. The N-terminal Met residue is removed by the protease systems present in E. coli, leaving Ser-Glu-Ala-Glu SEQ ID NO:16. The Glu-Ala-Glu amino acid sequence can be present or absent (we initiate experiments with Met-Ser-hIL21).

The protein was refolded and purified to 90-95% purity using conventional chromatographic methods.

The pure protein was subsequently N-terminally pegylated via reaction described in steps 1-5.

Subsequent purification was done using gelfiltration or size exclusion chromatography (SEC).

In an proliferation assay, the pegylated IL21 showed similar potentency to the unpegylated standard, indicating that the pegylation does not interfere with receptor binding, and that the reaction procedures are not harmful to the protein.

Pharmacological Methods

Proliferation assay using Baf-3(IL21R) cells.

IL3 dependent Baf-3 cells transfected with either the murine or the humane IL21R are grown in IL-3 containing culture medium until setup of a proliferation assay (preferably 3 days).

Cells used for the assay are washed in IL3-free medium and plated in 96 well-plates with 50.000 c/w in assay media (without IL-3). IL21 is added in serial dilutions from $10^{-7}$M-$10^{-13}$M and the cells incubated at 37° C., 5% $CO_2$. Alamar-Blue (Biosource) is added to all wells after 66 hours of culture and the cells incubated further for 6 hours. If cells are growing, the alamarBlue is reduced and the colour of the media changes from blue to red. Plates are then read on a Fluostar (bmg) at 550 nm (excitation) and 590 nm (emission) and analysed by Prism (GrafPad software).

A ref to Baf-3 cells:

Palacios, R. & Steinmetz, M. (1985) Cell 41 pp 727-734.

Description of a PEG-hIL-21 PK Study in Mice

The present experiment is to administer a single dose of PEG20K-hIL-21, PEG40K-hIL-21 and hIL-21 intravenously and subcutaneously to mice in order to obtain bioavailability and pharmacokinetics characteristics of PEG-hIL-21.

Material and Methods

Forty eight female C57BL/6Jbom weighing approximately 25 g from Bomholtgård, Ry, Denmark are included in the experiment.

During the study the animals will be kept and handled according to normal procedure in the animal unit (Standard Operating Procedure no. 010364) and are allowed free access to feed and water.

Test Formulations hIL-21, PEG20k-hIL-21 and PEG40k-hIL-21 at a concentration of 200 µg/ml. The test substances will be dissolved in PBS buffer pH 7.4.

Dosing

The test substance will be dosed according to the following:

20 µg/25 g mouse corresponding to 0.8 µg/g mouse weight.

The i.v. injections will be given in the tail vein in a volume of 0.1 ml.

The s.c. injections will be given on the back of neck in a volume of 0.1 ml.

Blood Samples

Blood samples will be collected according to the following schedule:

After intravenous injection:

Predose, 5, 10, 20, 30, 45 (minutes), 1, 1.5, 2, 4 and 6 hours after dosing.

After subcutaneous injection:

Predose, 10, 30 (minutes), 1, 1.5, 2, 3, 4, 6, 8 and 24 hours after dosing.

Blood samples will be drawn from the orbital venous plexus. Approximately 0.1-0.2 ml blood will be drawn at each sampling time. Three blood samples will be taken from each animal. Blood samples from two mice will be drawn at each time point.

Blood samples will be collected in Micronic test tubes and kept on ice for max 20 min before centrifugation (1200 m×g, 4° C., 10 min).

25 µl plasma sample will be transferred to Micronic tubes immediately after centrifugation and stored at −20° C. until analysis.

Assay

The plasma samples will be analysed for the content of hIL-21 by a specific immunoassay by Immunochemistry, Novo Nordisk A/S.

Plasma concentration-time profiles will be analysed by noncompartmental and compartmental pharmacokinetic methods.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

The invention claimed is:

1. A derivative of human interleukin 21 (IL-21) comprising
   (a) a human IL-21 polypeptide comprising (i) amino acid residues 32 to 162 of SEQ ID NO:2 or (ii) amino acid residues 30 to 162 of SEQ ID NO:2; and
   (b) one or more polymeric molecules linked to the N-terminus of the IL-21 polypeptide through a linker sequence of amino acids comprising Ser-Glu-Ala-Glu- (SEQ ID NO: 16).

2. The human IL-21 derivative of claim 1, comprising a linker sequence of amino acids comprising Met-Ser-Glu-Ala-Glu (SEQ ID NO: 17).

3. The derivative of claim 1, wherein the polymeric molecule is a polyethylene glycol (PEG) molecule.

4. The derivative of claim 3, wherein the PEG molecule has a molecular weight of 5 kDa and is linear or branched.

5. The derivative of claim 3, wherein the PEG molecule has a molecular weight of 10 kDa.

6. The derivative of claim 3, which comprisies 3-6 PEG molecules.

7. The derivative of claim 1, wherein the derivative of human IL-21 has a molecular weight of at least 50 kDa.

* * * * *

UNITED STATES PATENT AND TRADEMARK OFFICE
CERTIFICATE OF CORRECTION

PATENT NO. : 8,450,459 B2  
APPLICATION NO. : 12/189849  
DATED : May 28, 2013  
INVENTOR(S) : Bernd Peschke et al.

Page 1 of 1

It is certified that error appears in the above-identified patent and that said Letters Patent is hereby corrected as shown below:

On the Title Page:

Page 2, column 2 (Other Publications), line 16, delete "Fluorganic" and insert --Fluorogenic--, therefor.

In the Claims:

In Claim 6, column 61, line 19, delete "comprisies" and insert --comprises--, therefor.

Signed and Sealed this
Twenty-fifth Day of March, 2014

Michelle K. Lee
*Deputy Director of the United States Patent and Trademark Office*